(12) United States Patent
Vlaskamp et al.

(10) Patent No.: US 11,291,402 B2
(45) Date of Patent: Apr. 5, 2022

(54) METHOD AND APPARATUS FOR DETERMINING AN INDICATION OF COGNITIVE IMPAIRMENT

(71) Applicant: KONINKLIJKE PHILIPS N.V., Eindhoven (NL)

(72) Inventors: Bjorn Nicolaas Servatius Vlaskamp, Veldhoven (NL); Laura Klaming, Waalre (NL); Murray Fulton Gillies, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 388 days.

(21) Appl. No.: 16/348,654

(22) PCT Filed: Nov. 3, 2017

(86) PCT No.: PCT/EP2017/078113
§ 371 (c)(1),
(2) Date: May 9, 2019

(87) PCT Pub. No.: WO2018/086987
PCT Pub. Date: May 17, 2018

(65) Prior Publication Data
US 2020/0054269 A1   Feb. 20, 2020

Related U.S. Application Data

(60) Provisional application No. 62/420,181, filed on Nov. 10, 2016.

(30) Foreign Application Priority Data

Sep. 7, 2017   (EP) .................................... 17189923

(51) Int. Cl.
*A61B 5/00*   (2006.01)
*A61B 5/11*   (2006.01)
(Continued)

(52) U.S. Cl.
CPC .......... *A61B 5/4088* (2013.01); *A61B 5/1124* (2013.01); *A61B 5/162* (2013.01);
(Continued)

(58) Field of Classification Search
CPC ..... A61B 5/4088; A61B 5/1124; A61B 5/162; A61B 5/742; A61B 5/7475; A61B 5/165;
(Continued)

(56) References Cited

U.S. PATENT DOCUMENTS

| 7,211,050 B1 | 5/2007 | Caplygin |
| 2012/0330182 A1 | 12/2012 | Alberts |
| 2016/0100788 A1 | 4/2016 | Sano |

FOREIGN PATENT DOCUMENTS

| EP | 2438863 A1 | 4/2012 |
| WO | WO2004060164 A1 | 7/2004 |

(Continued)

OTHER PUBLICATIONS

Amodio et al. 'Variability of Trail Making Test, Symbol Digit Test and Line Trait Test in normal people. A normative study taking into account age-dependent decline and sociobiological variables' Aging Clin Exp Res, vol. 14, No. 2 pp. 117-131 2002 (Year: 2002).*

(Continued)

*Primary Examiner* — Patrick Fernandes

(57) ABSTRACT

According to an aspect, there is provided a computer-implemented method for determining an indication of visual attention/motoric dysfunction of a subject and/or an indication of executive cognitive dysfunction of the subject during or following a test comprising a plurality of targets that are to be completed by the subject, the method comprising the steps of receiving information on the time taken to complete each of the plurality of targets by the subject; determining a regression line for the subject based on the received information on the time taken to complete each of the plurality of targets and information on the time taken to complete each of the plurality of targets for a reference group of subjects; determining an indication of visual attention/motoric dysfunction of the subject based on a slope of the determined regression line and/or an indication of executive cognitive (Continued)

dysfunction of the subject based on an offset of the determined regression line; and outputting the indication of the visual attention/motoric dysfunction of the subject and/or the indication of the executive cognitive dysfunction of the subject.

20 Claims, 18 Drawing Sheets

(51) Int. Cl.
    *A61B 5/16*     (2006.01)
    *G16H 50/70*     (2018.01)
    *G16H 50/30*     (2018.01)
    *G16H 50/20*     (2018.01)
    *G16H 20/70*     (2018.01)

(52) U.S. Cl.
    CPC ............ *A61B 5/742* (2013.01); *A61B 5/7475* (2013.01); *G16H 20/70* (2018.01); *G16H 50/20* (2018.01); *G16H 50/30* (2018.01); *G16H 50/70* (2018.01)

(58) Field of Classification Search
    CPC .......... A61B 5/16; A61B 5/168; G16H 50/20; G16H 50/30; G16H 50/70; G16H 20/70
    See application file for complete search history.

(56) References Cited

FOREIGN PATENT DOCUMENTS

WO     WO2015067945 A1     5/2015
WO     WO-2016154658 A1 *   10/2016   ............. A61B 5/168

OTHER PUBLICATIONS

Narhi et al. 'Trail Making Test in Assessing Children with Reading Disabilities: A Test of Executive Functions or Content Information'; Perceptual and Motor Skills Jul. 1997, 84, 1355-1362 (Year: 1997).*

PCT International Search Report, International application No. PCT/EP2017/078113, dated Nov. 3, 2017.

Observations on the PCT International Search Report and the Written Opinion of International Application No. PCT/EP2017/078113, dated May 7, 2019.

Juarez J.M. et al., "Experiences on Computerised Neuropsychological Tests for Dementia Using a Mobile Touchable Interface", 2014 IEEE International Conference on Healthcare Informatics, IEEE Computer Science, pp. 335-361.

Tong T. et al., "Designing a Game-based Cognitive Assessment for a Tablet", Mechanical and Industrial Engineering, Jun. 2014.

Dahmen J. et al., "An Analysis of a Digital Variant of the Trail Making Test Using Machine Learning Techniques", Technol Health Care, 2017; 25(2): 251-264.

Fellows R.P. et al., "Multicomponent Analysis of a Digital Trail Making Test", US National Library of Medicine National Institutes of Health, The Clinical Neuropsychologist, Jan. 2017; 31(1): 154-167.

Poreh A. et al., "Decomposition of the Trail Making Test—Reliability and Validity of a Computer Assisted Method for Data Collection", Archives of Assessment Psychology, vol. 2 No. 1 (2012), Neuropsychological Assessment.

Schuepbach D. et al., "Determinants of Cerebral Hemodynamics During the Trail Making Test in Schizophrenia", ScienceDirect, Brain and Cognition,Nov. 2016, 106: pp. 96-104.

* cited by examiner

METHOD AND APPARATUS FOR DETERMINING AN INDICATION OF COGNITIVE IMPAIRMENT

CROSS-REFERENCE TO RELATED APPLICATIONS

This patent application claims the priority benefit under 35 U.S.C. § 371 of international patent application no. PCT/EP2017/078113, filed Nov. 3, 2017, which claims the benefit of U.S. Provisional Patent Application No. 62/420, 181, filed on Nov. 10, 2016, and which claims the benefit of European Patent Application No. 17189923.0, filed on Sep. 7, 2017, the contents of which are hereby incorporated by reference herein.

TECHNICAL FIELD OF THE INVENTION

The invention relates to a method and apparatus for determining an indication of cognitive impairment of the subject.

BACKGROUND TO THE INVENTION

The Trail Making Test (TMT) is a frequently used neuropsychological test that is used to assess various aspects of attention and executive cognitive functions. The TMT involves asking a subject to draw a line to connect dots together in the correct sequence. These dots, known as targets or elements, are typically printed on paper or displayed on a screen and the subject is given a pen or stylus and asked to connect them in the correct sequence. The TMT consists of two parts. Part A involves making (e.g. drawing) a trail or path between 25 numbered targets in ascending order. An example of Part A is shown in FIG. 1(a). Part B consists of 13 numbers and 12 letters which the subject is instructed to connect in an alternating pattern, e.g. 1, A, 2, B, 3, C, . . . .

The subject is asked to complete the trails as quickly as possible and completion time is measured as the main outcome of the tests. Clinical interpretation of performance on the TMT is based on part A mainly reflecting visual search/attention and motor speed skills and part B also requiring higher cognitive functions such as cognitive flexibility, task switching and working memory. Since part B is a more complex task, completion time is longer for part B than part A and the B/A ratio (the ratio of the time taken for part B to the time taken for part A) is a clinical outcome measure that is used to interpret a subject's executive function, with a higher score being indicative of impairment.

Currently, the only outcome measure used in clinical practice is the total completion time on part A and part B as well as scores derived from the total completion time on A and B such as the B/A ratio score.

SUMMARY OF THE INVENTION

There is a need for improvements in the assessment of tests performed by a subject, e.g. by adding new outcome measures to existing tests thereby increasing the information that can be extracted from the test, or by automating the scoring of tests. It is an object of the invention to provide an improved assessment of tests performed by the subject such as to determine, assess, infer or otherwise provide such outcome measures so that they could be used by a subject or care provider to improve the health condition of the subject.

Measuring the TMT digitally allows for measurement of completion time for each individual element (target) of the test. This can then be used to determine several new measures of the performance of the test by the subject, which can be used to provide an indication of visual attention/motoric dysfunction of a subject and/or an indication of executive cognitive dysfunction of the subject.

One such measure is based on a slope of a determined regression line formed using the completion times and/or an offset of the determined regression line which can provide separate indications of the subject's visual attention/motoric dysfunction and/or executive cognitive dysfunction.

Another such measure is referred to herein as inter-element variability (IEV) which relates to the variability of the time taken to complete certain targets and can provide more detailed information about the consistency of the subject's behavior.

Yet another measure is based on comparing the time taken to complete number targets to the time taken to complete letter targets which can provide an indication of the literary dysfunction of the subject.

According to a first aspect, there is provided a computer-implemented method for determining an indication of visual attention/motoric dysfunction of a subject and/or an indication of executive cognitive dysfunction of the subject during or following a test comprising a plurality of targets that are to be completed by the subject, the method comprising the steps of receiving information on the time taken to complete each of the plurality of targets by the subject; determining a regression line for the subject based on the received information on the time taken to complete each of the plurality of targets and information on the time taken to complete each of the plurality of targets for a reference group of subjects; determining an indication of visual attention/motoric dysfunction of the subject based on a slope of the determined regression line and/or an indication of executive cognitive dysfunction of the subject based on an offset of the determined regression line; and outputting the indication of the visual attention/motoric dysfunction of the subject and/or the indication of the executive cognitive dysfunction of the subject. It is an advantage of the invention to provide for the evaluation of individual element completion times, which enables the separation of two different cognitive processes (i.e. visual attentional processes/motoric processes vs. executive processes) and thus provides a more reliable measure of the functioning of a subject's visual attentional/motoric processes and their executive processes.

In some embodiments, the information on the time taken to complete each of the plurality of targets comprises, for each target, the time from the completion of the preceding target to the completion of said target.

In some embodiments, a target is completed when a marking device has entered the boundary of said target or the velocity of the marking device falls below a threshold in the vicinity of the target.

In some embodiments, completion of a target comprises the subject marking a path from said preceding target to said target on a test surface using a marking device.

In some embodiments, the test surface is e-paper, digital paper, a screen, or paper, and the marking device is a pen, stylus or digital pen. In some embodiments, the marking device can be controlled by the output of an eye-tracker or audio input.

In some embodiments, the information on the time taken to complete each of the plurality of targets for a reference group of subjects comprises, for each of the plurality of targets, an average of the time taken to complete said target by subjects in the reference group of subjects.

In some embodiments, the step of determining an indication of visual attention/motoric dysfunction of the subject based on a slope of the determined regression line comprises determining that the subject has a visual attention/motoric dysfunction if the slope of the regression line is greater than 1.

In some embodiments, the step of determining an indication of visual attention/motoric dysfunction of the subject comprises estimating the extent of the visual attention/motoric dysfunction of the subject based on the difference between the slope of the regression line and 1. It is an advantage of the invention to provide for a means to enable the determination of an indication of a visual attention/motoric dysfunction of the subject.

In some embodiments, the step of determining an indication of visual attention/motoric dysfunction of the subject comprises estimating the extent of the visual attention/motoric dysfunction of the subject based on the magnitude of the slope compared to a norm value and/or the magnitude of the slope compared to the variance of the time taken to complete each of the plurality of targets by the reference group of subjects.

In some embodiments, the step of determining an indication of executive cognitive dysfunction of the subject comprises determining that the subject has an executive cognitive dysfunction if the offset of the regression line is greater than 0.

In some embodiments, the step of determining an indication of executive cognitive dysfunction of the subject comprises estimating an extent of the executive cognitive dysfunction of the subject based on the magnitude of the offset. It is an advantage of the invention to provide for a means to enable the determination of an indication of an executive cognitive dysfunction of the subject.

In some embodiments, the step of determining an indication of executive cognitive dysfunction of the subject comprises estimating an extent of the executive cognitive dysfunction of the subject based on the magnitude of the offset compared to a norm value and/or the magnitude of the offset compared to the variance of the time taken to complete each of the plurality of targets by the reference group of subjects.

In some embodiments, the offset of the determined regression line is determined based on an average of the time taken to complete each of the plurality of targets by the reference group of subjects.

In some embodiments, the method further comprises the step of normalising the time taken to complete each of the plurality of targets by the subject using the information on the time taken to complete the corresponding target by the reference group of subjects to provide a set of normalised times. This normalisation allows for differences in the completion times due to, e.g. the layout of the targets, to be compensated, thereby allowing for more accurate indications of the visual attention/motoric dysfunction of the subject and executive cognitive dysfunction of the subject.

In some embodiments, the step of normalising comprises for each target, determining an average time taken to complete said target by the reference group of subjects; and dividing the time taken by the subject to complete said target by said determined average time taken.

In some embodiments, the method further comprises the step of determining a measure of the variability of the normalised times. It is an advantage of the invention to allow the measure of the variability of the normalised times so as to provide information about the consistency of the subject's behaviour.

In some embodiments, the method further comprises the step of determining the measure of variability of the normalised times for a first test by the subject; determining a measure of variability of the normalised times for a second test by the subject; and determining a further indication of the visual attention/motoric dysfunction of a subject and/or a further indication of executive cognitive dysfunction of the subject from a comparison of the determined measure of variability of the normalised times for the first test and determined measure of variability of the normalised times for the second test.

In some embodiments, the plurality of targets comprises a set of number targets and a set of letter targets; and the method further comprises the step of determining an indication of a literary dysfunction of the subject based on a comparison of the time taken to complete each of the set of number targets and the time taken to complete each of the set of letter targets. An advantage of the invention, in addition to providing indications of visual attention/motoric dysfunction and/or executive cognitive dysfunction, is to enable the use of the completion times to provide an indication of literary dysfunction.

In some embodiments, the step of determining an indication of a literary dysfunction of the subject comprises determining an average time taken to complete each of the set of number targets; determining an average time taken to complete each of the set of letter targets; and determining the indication of the literary dysfunction of the subject based on the difference between the determined averages.

In some embodiments, the step of determining the indication of the literary dysfunction of the subject comprises comparing the difference between the determined averages to the difference between averages for the reference group of subjects. It is an advantage of the invention to provide for a comparison between the subject's literary function/dysfunction and that of a reference population.

In some embodiments, the step of determining an indication of a literary dysfunction of the subject comprises determining an average time taken to complete each of the set of number targets; determining an average time taken to complete each of the set of letter targets; and determining the indication of the literary dysfunction of the subject based on a ratio of the determined averages.

In some embodiments, the step of determining the indication of the literary dysfunction of the subject comprises comparing the ratio of the determined averages to a ratio of averages for the reference group of subjects.

In some embodiments, the plurality of targets comprises a set of numbers and a set of letters.

According to a second aspect, there is provided a computer program product comprising a computer readable medium having computer readable code embodied therein, the computer readable code being configured such that, on execution by a suitable computer or processor, the computer or processor is caused to perform any of the methods or method steps described above.

According to a third aspect, there is provided an apparatus for determining an indication of visual attention/motoric dysfunction of a subject and/or an indication of executive cognitive dysfunction of the subject during or following a test comprising a plurality of targets that are to be completed by the subject, the apparatus comprising a processing unit that is configured to receive information on the time taken to complete each of the plurality of targets by the subject;

determine a regression line for the subject based on the received information on the time taken to complete each of the plurality of targets and information on the time taken to complete each of the plurality of targets for a reference group of subjects; determine an indication of visual attention/motoric dysfunction of the subject based on a slope of the determined regression line and/or an indication of executive cognitive dysfunction of the subject based on an offset of the determined regression line; and output the indication of the visual attention/motoric dysfunction of the subject and/or the indication of the executive cognitive dysfunction of the subject. It is an advantage of the invention to provide for the evaluation of individual element completion times, which enables the separation of two different cognitive processes (i.e. visual attentional processes/motoric processes vs. executive processes) and thus provides a more reliable measure of the functioning of a subject's visual attentional/motoric processes and their executive processes.

Various embodiments of the apparatus are also contemplated in which the processing unit is further configured to perform any of the methods or method steps described above.

In some embodiments, the apparatus further comprises a display screen for displaying the plurality of targets to the subject; and a user interface for receiving an input from the subject to complete one or more of the plurality of targets.

In some embodiments, the display screen and the user interface are a touchscreen.

In alternative embodiments, the apparatus further comprises a receiver for receiving the information on the time taken to complete each of the plurality of targets by the subject from an electronic device.

In some embodiments, the information on the time taken to complete each of the plurality of targets comprises, for each target, the time from the completion of the preceding target to the completion of said target.

In some embodiments, a target is completed when a marking device has entered the boundary of said target or the velocity of the marking device falls below a threshold in the vicinity of the target.

In some embodiments, completion of a target comprises the subject marking a path from said preceding target to said target on a test surface using a marking device.

In some embodiments, the test surface is a capacitance touchscreen, a resistive touchscreen or a acoustic pulse reconition touchscreen.

In some embodiments, the marking device is a finger of the subject.

In some embodiments, the test surface is e-paper, digital paper, a screen, or paper, and the marking device is a pen, stylus or digital pen. In some embodiments, the marking device can be controlled by the output of an eye-tracker or audio input.

In some embodiments, the information on the time taken to complete each of the plurality of targets for a reference group of subjects comprises, for each of the plurality of targets, an average of the time taken to complete said target by subjects in the reference group of subjects.

In some embodiments, the processing unit is configured to determine an indication of visual attention/motoric dysfunction of the subject based on a slope of the determined regression line by determining that the subject has a visual attention/motoric dysfunction if the slope of the regression line is greater than 1.

In some embodiments, the processing unit is configured to determine an indication of visual attention/motoric dysfunction of the subject by estimating the extent of the visual attention/motoric dysfunction of the subject based on the difference between the slope of the regression line and 1. It is an advantage of the invention to provide for a means to enable the determination of an indication of a visual attention/motoric dysfunction of the subject.

In some embodiments, the processing unit is configured to determine an indication of visual attention/motoric dysfunction of the subject by estimating the extent of the visual attention/motoric dysfunction of the subject based on the magnitude of the slope compared to a norm value and/or the magnitude of the slope compared to the variance of the time taken to complete each of the plurality of targets by the reference group of subjects.

In some embodiments, the processing unit is configured to determine an indication of executive cognitive dysfunction of the subject by determining that the subject has an executive cognitive dysfunction if the offset of the regression line is greater than 0.

In some embodiments, the processing unit is configured to determine an indication of executive cognitive dysfunction of the subject by estimating an extent of the executive cognitive dysfunction of the subject based on the magnitude of the offset. It is an advantage of the invention to provide for a means to enable the determination of an indication of an executive cognitive dysfunction of the subject.

In some embodiments, the processing unit is configured to determine an indication of executive cognitive dysfunction of the subject comprises estimating an extent of the executive cognitive dysfunction of the subject based on the magnitude of the offset compared to a norm value and/or the magnitude of the offset compared to the variance of the time taken to complete each of the plurality of targets by the reference group of subjects.

In some embodiments, the processing unit is configured to determine the offset of the determined regression line based on an average of the time taken to complete each of the plurality of targets by the reference group of subjects.

In some embodiments, the processing unit is further configured to normalise the time taken to complete each of the plurality of targets by the subject using the information on the time taken to complete the corresponding target by the reference group of subjects to provide a set of normalised times. This normalisation allows for differences in the completion times due to, e.g. the layout of the targets, to be compensated, thereby allowing for more accurate indications of the visual attention/motoric dysfunction of the subject and executive cognitive dysfunction of the subject.

In some embodiments, the processing unit is configured to normalise by, for each target, determining an average time taken to complete said target by the reference group of subjects; and dividing the time taken by the subject to complete said target by said determined average time taken.

In some embodiments, the processing unit is further configured to determine a measure of the variability of the normalised times. The measure of the variability of the normalised times can be used to provide information about the consistency of the subject's behaviour.

In some embodiments, the processing unit is further configured to determine the measure of variability of the normalised times for a first test by the subject; determine a measure of variability of the normalised times for a second test by the subject; and determine a further indication of the visual attention/motoric dysfunction of a subject and/or a further indication of executive cognitive dysfunction of the subject from a comparison of the determined measure of variability of the normalised times for the first test and determined measure of variability of the normalised times for the second test.

In some embodiments, the plurality of targets comprises a set of number targets and a set of letter targets; and wherein the processing unit is further configured to determine an indication of a literary dysfunction of the subject based on a comparison of the time taken to complete each of the set of number targets and the time taken to complete each of the set of letter targets. An advantage of the invention, in addition to providing indications of visual attention/motoric dysfunction and/or executive cognitive dysfunction, is to enable the use of the completion times to provide an indication of literary dysfunction.

In some embodiments, the processing unit is configured to determine an indication of a literary dysfunction of the subject by determining an average time taken to complete each of the set of number targets; determining an average time taken to complete each of the set of letter targets; and determining the indication of the literary dysfunction of the subject based on the difference between the determined averages and/or based on a ratio of the determined averages.

In some embodiments, the processing unit is configured to determine the indication of the literary dysfunction of the subject by comparing the difference between the determined averages to the difference between averages for the reference group of subjects and/or comparing the ratio of the determined averages to a ratio of averages for the reference group of subjects. It is an advantage of the invention to provide for a comparison between the subject's literary function/dysfunction and that of a reference population.

In some embodiments, the plurality of targets comprises a set of numbers and a set of letters.

According to a fourth aspect, there is provided a computer-implemented method for analysing the result of a test comprising a plurality of targets that are to be completed by the subject, the method comprising the steps of receiving information on the time taken to complete each of the plurality of targets by the subject; receiving information on the time taken to complete each of the plurality of targets for a reference group of subjects; normalising the time taken to complete each of the plurality of targets by the subject using the information on the time taken to complete the corresponding target by the reference group of subjects to provide a set of normalised times; determining a measure of the variability of the normalised times; and outputting the measure of the variability of the normalised times. This normalisation allows for differences in the completion times due to, e.g. the layout of the targets, to be compensated, thereby providing an improved indication of the cognitive function of the subject.

According to a fifth aspect, there is provided a computer program product comprising a computer readable medium having computer readable code embodied therein, the computer readable code being configured such that, on execution by a suitable computer or processor, the computer or processor is caused to perform the method according to the fourth aspect.

According to a sixth aspect, there is provided an apparatus for for analysing the result of a test comprising a plurality of targets that are to be completed by the subject, the apparatus comprising a processing unit configured to receive information on the time taken to complete each of the plurality of targets by the subject; receive information on the time taken to complete each of the plurality of targets for a reference group of subjects; normalise the time taken to complete each of the plurality of targets by the subject using the information on the time taken to complete the corresponding target by the reference group of subjects to provide a set of normalised times; determine a measure of the variability of the normalised times; and output the measure of the variability of the normalised times. This normalisation allows for differences in the completion times due to, e.g. the layout of the targets, to be compensated, thereby providing an improved indication of the cognitive function of the subject.

According to a seventh aspect, there is provided a computer-implemented method for determining an indication of literary dysfunction of a subject following a test comprising a plurality of targets that are to be completed by the subject, wherein the plurality of targets comprises a set of number targets and a set of letter targets, the method comprising the steps of receiving information on the time taken to complete each of the plurality of targets by the subject; determining an indication of a literary dysfunction of the subject based on a comparison of the time taken to complete each of the set of number targets and the time taken to complete each of the set of letter targets; and outputting the indication of the literary dysfunction of the subject.

According to an eighth aspect, there is provided a computer program product comprising a computer readable medium having computer readable code embodied therein, the computer readable code being configured such that, on execution by a suitable computer or processor, the computer or processor is caused to perform the method according to the seventh aspect.

According to a ninth aspect, there is provided an apparatus for determining an indication of literary dysfunction of a subject following a test comprising a plurality of targets that are to be completed by the subject, wherein the plurality of targets comprises a set of number targets and a set of letter targets, the apparatus comprising a processing unit configured to receive information on the time taken to complete each of the plurality of targets by the subject; determine an indication of a literary dysfunction of the subject based on a comparison of the time taken to complete each of the set of number targets and the time taken to complete each of the set of letter targets; and output the indication of the literary dysfunction of the subject.

These and other aspects of the invention are apparent from and will be elucidated with reference to the embodiments described hereinafter.

It will be appreciated by those skilled in the art that two or more of the above-mentioned options, implementations, and/or aspects of the invention may be combined in any way deemed useful.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE PREFERRED EMBODIMENTS

As noted above, it is desired to provide improvements in the assessment of the performance of tests, such as trail making tests (TMTs), in which a subject is to complete an activity in which they have to select or connect a plurality of targets (also refered to as elements) as quickly and accurately as possible. A target will be understood as any visible area or region that a user has to hit, highlight, cancel or otherwise select. It will be appreciated that although the invention is described with reference to the Trail Making Test (TMT), the invention is more generally applicable to any type of test, game or (more generally) activity in which a participant or subject has to specify a path to join, connect, cancel or select a plurality of targets as quickly as possible.

It should be noted that the 'subject' referenced herein is the person or individual that is taking part in the activity or test.

It will be appreciated from the following description of the invention that it is applicable to an electronic implementation of a test, game or activity where a plurality of targets are shown or projected on a display screen (or a paper copy of a test is overlaid on the display screen), and the subject uses a user interface of the electronic device to input or specify a line or path that connects the targets. In these embodiments the user interface can include a computer mouse, a touchpad or a touchscreen that allows the subject to specify the line using their finger or an object, such as a stylus. It will also be appreciated that the invention is applicable to the assessment of a test performed using pen and paper, provided that information on the timing of the completion of each of the targets is available. For example, such information can be obtained from a video sequence of the completion of the test by the subject.

Figure 2:
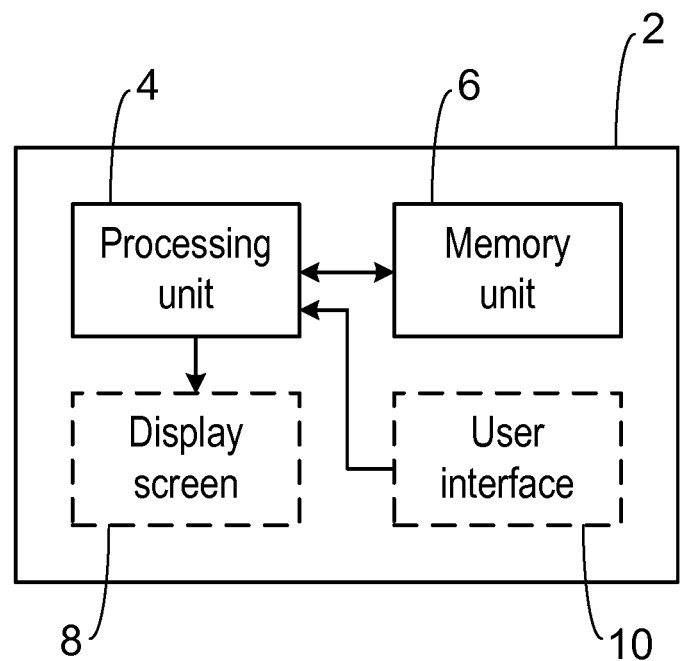
FIG. 2 is a block diagram of an exemplary apparatus according to an embodiment of the invention.

FIG. 2 shows a block diagram of an exemplary apparatus that can be used to assess or analyse the performance of the test according to an embodiment of the invention. In some embodiments, the apparatus can also be used by the subject to perform or complete the test. The apparatus 2 is an electronic device that comprises a processing unit 4 and a memory unit 6. The processing unit 4 is configured or adapted to control the operation of the apparatus 2 and to implement the techniques according to the invention for assessing the performance of the test by the subject and determining an indication of visual attention/motoric dysfunction of the subject and/or an indication of executive cognitive dysfunction of the subject.

The processing unit 4 can be implemented in numerous ways, with software and/or hardware, to perform the required function(s). The processing unit 4 may comprise one or more microprocessors that may be programmed using software to perform the required functions. The processing unit 4 may be implemented as a combination of dedicated hardware to perform some functions and a processor (e.g., one or more programmed microprocessors and associated circuitry) to perform other functions. Examples of components that may be employed in various embodiments of the present disclosure include, but are not limited to, conventional microprocessors, application specific integrated circuits (ASICs), and field-programmable gate arrays (FPGAs).

The memory unit 6 can store program code that can be executed by the processing unit 4, and for example computer code that can cause or allow the processing unit 4 to implement the techniques according to the invention. The memory unit 6 can also or alternatively store information required during the implementation of the techniques according to the invention, for example information on the plurality of targets, the subject-specified path, and/or the results of any assessment or evaluation of the subject-specified path. The memory unit 6 can also or alternatively store information on the results of tests previously completed by the subject or other subjects (e.g. a reference population) for comparison with the results of the current test. The memory unit 6 can comprise any suitable type of non-volatile or volatile memory, including, but not limited to, magnetic-based storage, such as a hard disk, solid-state memory, or optical-based storage, such as an optical disk.

As noted above, the apparatus 2 is for assessing or analysing the the performance of a test by a subject. In some embodiments, the apparatus 2 can also be used to provide the electronic implementation of the test, game or activity where a plurality of targets are shown or projected on a display screen 8 of the apparatus 2 (which is also referred to as a test surface, i.e. a surface on which the test is performed), and the subject uses a user interface 10 of the apparatus 2 to input or specify a line or path that connects the displayed targets. In these embodiments the user interface 10 can include any suitable type of device or component that allows a subject to specify the line or path, such as a computer mouse, a touchpad or a touchscreen (in which case the display screen 8 and user interface 10 are effectively implemented by the same component). In the case of a touchscreen, the subject may be able specify or draw the line using their finger, or alternatively the subject can use an object, such as a stylus, digital pen or, to draw the line on the touchscreen.

Alternatively, the apparatus 2 may receive information on the performance of the test, such as the time taken to complete each target (or information on the performance of the test from which the time taken to complete each target can be derived), from another device (e.g. a test apparatus), in which case this data can be stored in the memory unit 6 for subsequent processing or provided directly to the processing unit 4. In these embodiments, the test, game or activity can be presented to the subject using an electronic device (e.g. a tablet, smartphone, laptop or computer), and the results of the test, game or activity can be communicated to the apparatus 2 for evaluation. In this case, the apparatus 2 can be a computer or other type of electronic device (e.g. a server) that is located remotely from the user, and that could, for example, be used by an assessor, e.g. a healthcare professional, and that can comprise a receiver for receiving the information from the electronic device.

In either case, the apparatus 2 may also include a component or components for outputting a result of the test, or an indication of the performance of the test to the subject or other party (e.g. a healthcare professional). In some embodiments the indication can be output visually using the display screen 8, or audibly using another component, such as a speaker, etc.

Figure 3:
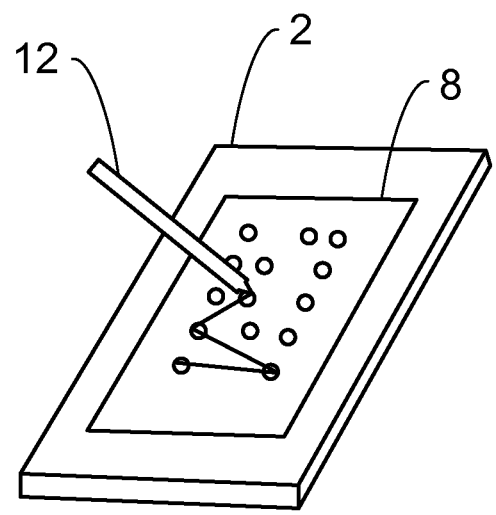
FIG. 3 is an illustration of an apparatus in the form of a tablet.

FIG. 3 is an illustration of an apparatus 2 in the form of a tablet. The tablet 2 comprises a test surface/display screen (touchscreen) 8 on which a plurality of targets can be displayed to the subject, and the subject is provided with a stylus or digital pen 12 to draw a path connecting or joining the targets together. It will be appreciated that the apparatus 2 may comprise a digitser for receiving/measuring the stylus/pen 12 movements on the test surface/display screen 8. The processing unit 4 in the tablet 2 can evaluate the path (trail) input by the subject onto the touchscreen 10, or alternatively the tablet 2 can communicate information on the path input by the subject and the plurality of targets to a remote apparatus 2. In the former embodiment, the technique according to the invention can be implemented as part of an application (app) that can be installed on the tablet 2.

It will be appreciated that the apparatus 2 can take alternative forms, for example a smart phone, a laptop, a desktop computer, a television, etc., and FIG. 3 should not be considered limiting.

As described above, an assessment of the performance of a TMT is typically based on the total time taken to complete the part A test, the total time taken to complete the part B test, and derived measures such as the ratio of these two completion times. However, in accordance with the invention, new measures are defined that are based on the time taken to complete each of the targets. The time taken to complete each target is described below with reference to FIG. 4, which illustrates part of a path drawn by a user in a Trail Making Test. The time taken to complete each target is also referred to as the 'target completion time' or 'completion time' herein.

Figure 4:
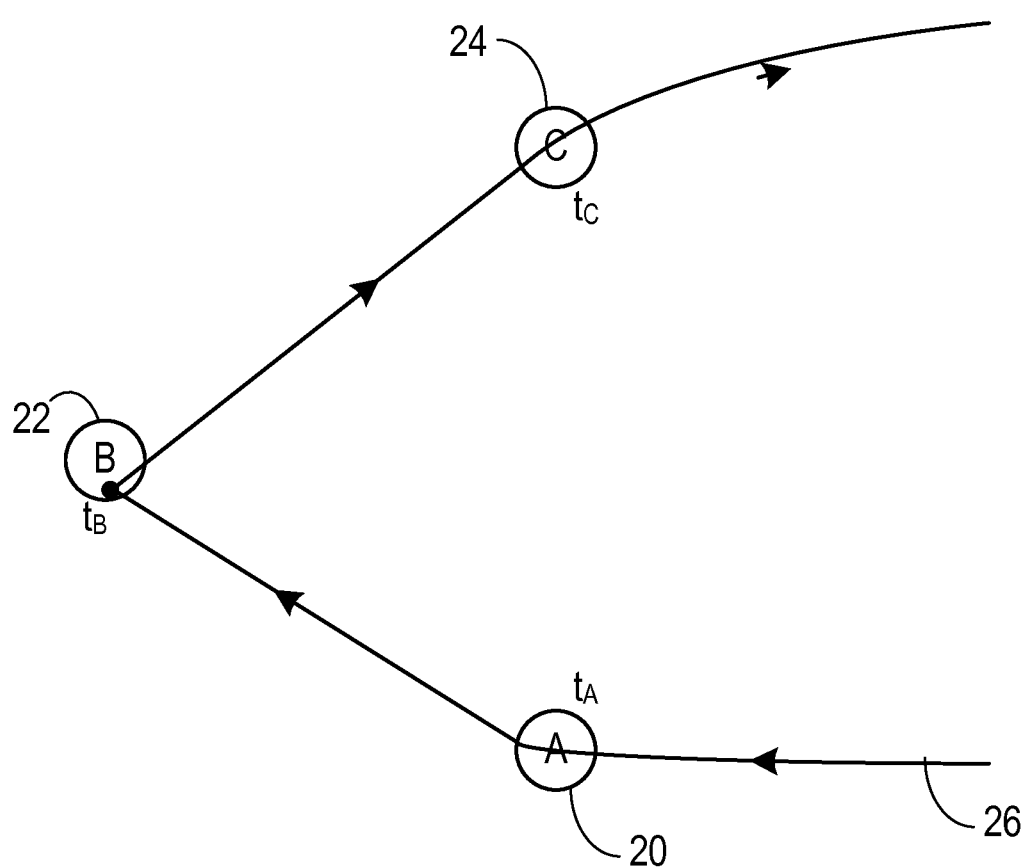
FIG. 4 is an illustration of a subject specified-path in part of a Trail Making Test.

In FIG. 4 three targets are shown, Target A 20, Target B 22 and Target C 24, and the targets are to be hit or selected in that order (i.e. Target A followed by Target B followed by Target C). In FIG. 4 the subject-specified path 26 crosses Target A 20 at time $t_A$ (i.e. Target A is correctly hit or selected at time $t_A$), moves towards Target B 22 and hits Target B at time $t_B$, and then move towards, and crosses, Target C 24 at time $t_C$.

The time taken to complete a particular target is the time from the completion of the preceding target to the completion of that target. It will be appreciated that the completion time for any target will typically comprise time in which the subject is searching the test for the next target and then the time taken to draw the path to the next target.

The time at which a target is completed can be the time at which the subject-specified path crosses the boundary of the target, or it can be the time at which the subject starts to 'dwell' on a target (which can be determined as the time that the velocity of the path generation (e.g. the velocity of the pen or stylus) falls below a threshold value). In the latter case, it can be assumed that processing (particularly visual) of the next target by the subject starts as soon as the pen/stylus starts to 'dwell' on the previous target.

In the example of FIG. 4, the time taken to complete Target B 22 is given by $t_B-t_A$, and the time taken to complete Target C 24 is given by $t_C-t_B$. A completion time can be determined for each of the targets in the test. In the case of a TMT A or TMT B that each comprise 25 elements or targets, a respective completion time will be determined for each of the 25 targets.

Figure 5:
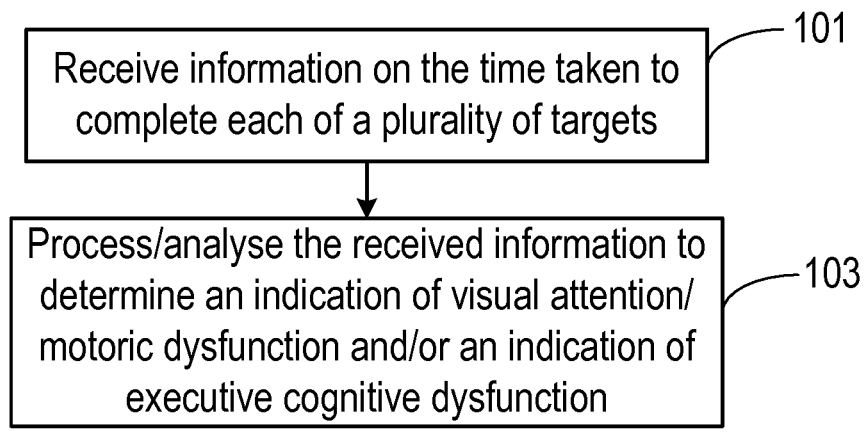
FIG. 5 is a flow chart illustrating a general method according to an aspect of the invention.

The flow chart in FIG. 5 illustrates a method of determining an indication of visual attention/motoric dysfunction of a subject and/or an indication of executive cognitive dysfunction of the subject according to an aspect. The indication can be derived from the results of a test that comprises a plurality of targets that a subject is to complete, such as a Trail Making Test (part A and/or part B), although it will be appreciated that the method is applicable to other types of test.

The method can be implemented by apparatus 2, for example by processing unit 4. It will be appreciated from the above that the invention can be applied in real time (i.e. as the subject is specifying the path to connect the targets), or applied once the subject has completed the test.

In step 101, information on the time taken to complete each of a plurality of targets is received. This information is referred to as completion time information. This information can be in the form of a time value for each of the targets, or a time at which each target was completed (from which the time taken to complete each target can be derived).

Depending on the implementation of the apparatus 2, the information can be obtained from the memory unit 6, obtained from a user interface component 10 (e.g. touch screen), and/or obtained from a digital camera that is used to observe the path specified by the subject in performing the test (e.g. on a paper or electronic version of the test).

It will be appreciated that where the test is implemented electronically (i.e. the targets are displayed on a display screen 8), the method prior to step 101 can comprise displaying the plurality of targets on a display screen 8 and step 101 can comprise receiving an input from a subject specifying a path via a user interface 10. The subject-specified path will also be shown on the display screen 8.

Next, in step 103, the received information is processed or analysed to determine an indication of visual attention/motoric dysfunction of the subject and/or an indication of executive cognitive dysfunction of the subject. In some embodiments, step 103 makes use of population data that comprises information on the time taken to complete the plurality of targets by a reference group of subjects. In this case, the method can further comprise receiving completion time information for the reference group of subjects. This information can be stored in the memory unit 6, or it can be stored remotely from the apparatus 2, for example in a remote server or database.

In some embodiments, the completion time information for the subject can be compared to the completion time information for the reference group of subjects. In other embodiments, the completion time information for the reference group of subjects can be used to normalise the completion time information for the subject.

Various embodiments and implementations of step 103, and in particular various indications and/or parameters that can be determined from the received completion time information are described in more detail below.

Inter-Element Variability

A first indication that can be determined is referred to herein as "inter-element variability" (IEV) which relates to the variability of the time taken to complete certain targets and can provide more detailed information about the consistency of the subject's behavior.

Inter-element variability is a measure which is analogous to intra-individual variability (IIV) in computerized reaction time tests from experimental psychology. In these tests, participants have to respond as quickly and accurately as possible to stimuli, mostly visual stimuli appearing on a computer screen, for multiple trials. The reaction time variability within an individual is the IIV and is mostly quantified as the range spanning the central 80% of the reaction time distribution. As noted above, currently, the TMT performance is quantified as the completion time on the TMT A and TMT B or derivatives of those completion times such the TMT B/TMT A ratio. These scores only provide limited information about the cognitive abilities of the subject. Currently, neuropsychologists often include qualitative observations in their diagnosis but do not have any further quantitative information about TMT performance available to them.

Thus, IEV provides additional quantitative information, and there are two main advantages of using this measure. Firstly, IIV is considered an informative measure of cognitive functioning and may be even more informative than overall reaction times. Indeed, IIV is more highly correlated to cognitive dysfunctioning than reaction time/completion time when subjects have to do cognitively demanding tasks which require manipulating information in working memory and tasks which require subjects to switch cognitive sets. These are exactly the domains that are tested with the TMT and therefore IEV may provide more information about the subject's cognitive functioning. Secondly, during the TMT the neuropsychologist may observe inconsistent behavior of the subject while at the same time the subject has normal TMT completion times. Using IEV, the neuropsychologist has a quantitative measure for this observation to refer to for their diagnosis.

By determining the IEV on the TMT B it is possible to identify the consistency of the subject's behaviour on the TMT B compared to the TMT A as well as compared to norm data on IEV.

Figure 1B:
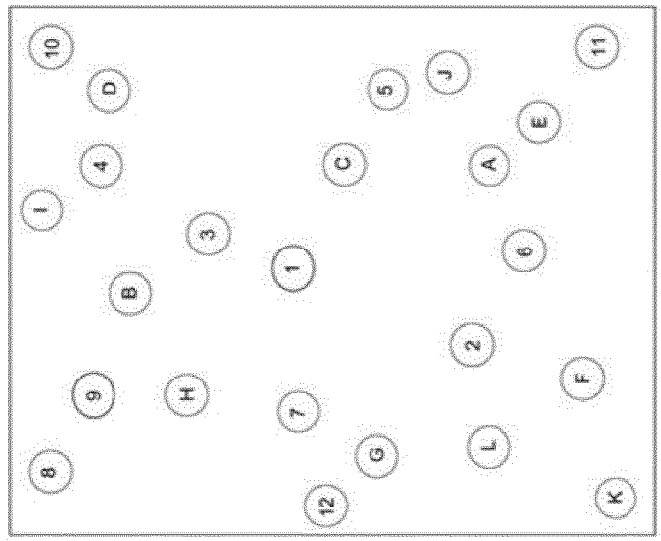
FIGS. 1(a) and 1(b) show examples of a Trail Making Test.
Figure 1A:
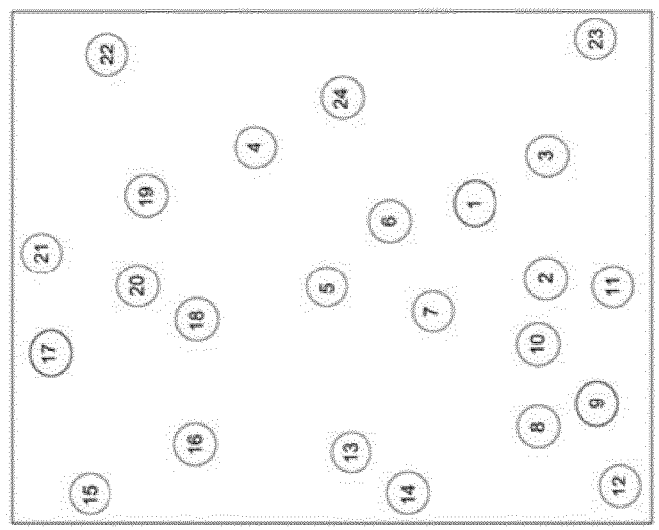

In some embodiments, to determine the IEV for a subject, the completion times for the subject are normalized per element/target. Completion times are different per element because they are differently situated within the TMT, as shown in FIG. 1. Some elements are far apart, some are visually crowded, etc. These factors have a significant effect on the completion time for a particular element/target. One way to normalize the element/target completion time of a subject is by dividing it by the median element completion time for a reference group of people. That is, the median of the times taken by a reference group of subjects to complete that element/target (or alternatively another representative measure or average of the time taken to complete that element/target, such as the mean, mode, etc.) is determined, and the time taken by the subject to complete that element/target is divided by that representative measure.

In some embodiments, to compensate for errors by the subject in completing the test (e.g. cancelling the wrong target or not correctly following the instructions for the test), when determining the IEV for the subject the completion times for any targets that were not cancelled or completed in the correct sequence or order can be removed from the completion time data. In some cases, the time for the target that was completed incorrectly can be replaced with a norm time for that target (i.e. the average time taken to complete that target by a population of subjects).

Next, IEV is calculated across the 24 element cancellations within a single TMT. In analogy to IIV, the IEV can be the difference between the 10% and 90% cuts through the distribution of element completion times of the subject. However, other measures of variance could be used.

The determined IEV value can be output by the apparatus 2 to the subject or to a neuropsychologist.

Thus, IEV can be calculated similar to the way IIV (inter-item variability) is calculated in reaction time tasks with multiple successive items to respond to. In more detail, a distribution should be compiled of the completion times for all elements on the TMT B (resulting in distributions of 25 completion times). This can be done by applying different methods. Next, for each subject, the IEV can be calculated as the difference between the 10% and 90% (or other) cuts through the distribution. It will be appreciated that other measures of variability may be used as well, such as standard deviation. Because completion times are determined by the subject but also by element characteristics (e.g. the time needed to find visual information is dependent on its visual eccentricity and the distance to neighboring information), they are first normalized as described above. Normalization can be done by dividing each individual element completion time by the median completion time for each element across a large sample of healthy participants (which can preferably be matched to the subject at least in age (or age range), handedness (i.e. which hand does the subject write with (also known as the dominant hand) and/or which hand was used for the test) and/or education level). These normalized completion times are then used to calculate the IEV. It will be appreciated that other normalization methods can be applied as well.

Figure 6:
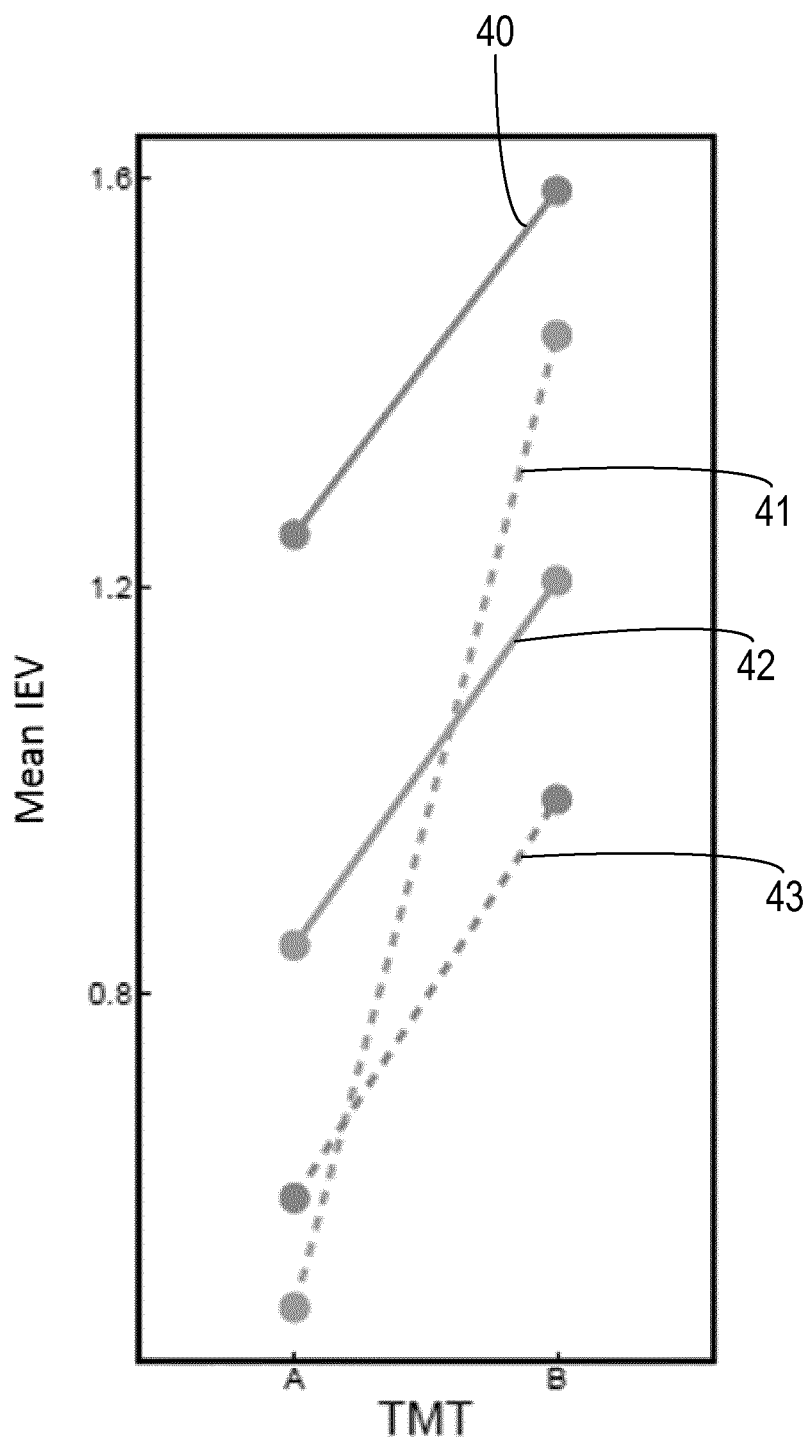
FIG. 6 is a graph illustrating the mean inter-element variability (IEV) for the TMT A and TMT B tests.

Based on research data from 82 healthy subjects, the IEV for the TMT A and B was determined. Half of the sample group performed the TMT with their dominant hand and the other half performed the TMT with their non-dominant hand. A significant interaction between condition (dominant vs. non-dominant hand) and TMT A completion time was found, so the group was divided based on a median split on their TMT A completion time to produce a fast TMT A group and a slow TMT A group. It was found that three of the four groups show consistent behavior as expressed by the IEV on the TMT A and the IEV on the TMT B, while one of the groups did not show consistent behavior which may indicate that their behavior may be due to specific attentional problems or compromised executive control. In the sample, the problem is likely due to compromised executive control since the group that behaved inconsistently is one of the two groups that performed the TMT with their non-dominant hand, which is believed to have compromised their executive control. The results are plotted in FIG. 6, which shows the mean IEV for the two TMT tests, A and B, for the four groups: a slow TMT group that used their dominant hand (line 40), a fast TMT group that used their non-dominant hand (line 41), a slow TMT group that used their non-dominant hand (line 42) and a fast TMT group that used their dominant hand (line 43). As can be seen in FIG. 6, the slopes are very similar for the dominant hand-fast TMT A (line 43), the dominant hand-slow TMT A (line 40) and the non-dominant hand-slow TMT A (line 42) groups, whereas the slope of the non-dominant hand-fast TMT A group (line 41) differs.

In clinical practice, IEV could be used as an additional outcome measure when determining a subject's IEV and comparing it to the IEV norms for the TMT. If a subject's IEV differs from the IEV norms (similar to the slope of the non-dominant hand-fast TMT A group as shown in FIG. 6), this can be an indication of additional problems or could help specify the subject's cognitive problems.

Separate Evaluation of Executive and Lay-Out Related Cognitive Processes

Another measure that can be determined from the completion times allows separate indications of the subject's visual attention/motoric dysfunction and/or executive cognitive dysfunction to be obtained. In particular, this measure is based on a slope of a regression line formed using the completion times and/or an offset of a regression line.

The TMT is often performed as part of a battery of tests. It would be valuable to include as few tests as possible in the assessment of the patient as that would save time and be less exhausting for the patient. Although TMT part B and TMT part A are assumed to be identical in terms of visual attentional load and in terms of motoric processes, this is not the case. This difference may or may not be important depending on the subject. In current clinical practice using the paper-pencil format of the TMT however, there is no way of discerning what the impact of this difference is on an individual subject's performance. The above measure provides another way of assessing performance for visual attentional processes/motoric processes and executive functioning separately and can be therefore provide a 'second opinion' in addition to the TMT A-B comparison. Separating these two different cognitive processes (i.e. visual attentional processes/motoric processes vs. executive processes) by evaluating individual element completion times provides a more reliable measure of the functioning of a subject's visual attentional/motoric processes and their executive processes. This measure can be calculated as follows. In addition to the completion time data for the subject, a reference data set is required that contains completion time data or TMT test results in another format (e.g. a video of the test or raw data from the data input element, such as a touch-screen) for a number of subjects. A data set is needed of healthy subjects that at least match the subject's age, education level, and/or handedness (i.e. which hand the subject writes with (also known as the dominant hand) and/or which hand was used for the test). Where the reference data is not provided in the form of completion times, the data will need to be processed to calculate element completion times.

The subject's completion time data is compared to the completion time data of the reference group. In particular embodiments, a regression is calculated of the subject element completion times on the reference group completion times.

The slope (gradient) of the line provides an indication of whether the subject has a visual attention/motoric dysfunction. A slope>1 is an indication of visual attention/motoric dysfunction. The offset of the line provides an indication of whether the subject has an executive cognitive dysfunction. The offset can be calculated at the middle of the range of the element completion times of the reference group. An offset>0 is an indication of executive dysfunctioning.

A question that neuropsychologist may want to address is whether layout related processes caused a slow TMT B performance. One way to determine this is to do an analysis of the subject's completion time data by comparing a first (linear) model:

$$Y = a + X \qquad (1)$$

with fixed slope (slope=1) and offset, a, as a free parameter, to a second model which includes slope, b, as a free parameter $$Y = a + bX \qquad (2)$$

using an F-test, or other form of statistical analysis technique. If the second model in equation (2) predicts the completion time data significantly better (more explained variance) than the first model in equation (1) and the slope b is larger than 1, then layout related processes contributed in a disproportionate way to the slow performance. Equations (1) and (2) are both regression equations.

As set out above, the TMT is primarily used to test executive functions such as cognitive flexibility by comparing TMT A and B completion times. The TMT B introduces a set-switching task which causes an increment in completion time relative to the TMT A and has increased working memory demands. By comparing the completion time on each individual element/target to the average or median completion time on those elements for a reference group of subjects, it is possible to infer whether a subject's performance is primarily determined by visual attentional/motoric processes or by executive processes. To be able to do so, it can be assumed that the contribution of executive processes to each element completion is uniformly distributed across all elements, whereas the contribution of visual attentional/motoric processes to the completion time depends on the exact spatial visual configuration of each element. The elements are quasi randomly dispersed over the TMT, which leads to varying distances between subsequent elements and also leads to some elements being surrounded by many other elements whereas others are situated relatively in isolation. These two factors (distance between subsequent elements and element crowding) have a major impact on visual attention/motoric processes.

Longer element completion times on the TMT B are caused by more visual attentional/motoric processing demands than shorter element completion times. By comparing the performance of a subject on each element to a reference group of healthy subjects, an assessment can be made of failure in these areas: if the subject's performance varies across elements in a way similar to that of the reference group of subjects there is no deficit. However, if the subject performs disproportionally bad on elements which already require a long time to complete in the reference group, this is evidence of a deficit in visual attentional/motoric processes. For executive functions, a different logic holds. Since executive functions require the same amount of time per element, a deficit should become apparent as a constant offset in completion times across all elements of the TMT B.

Figure 7:
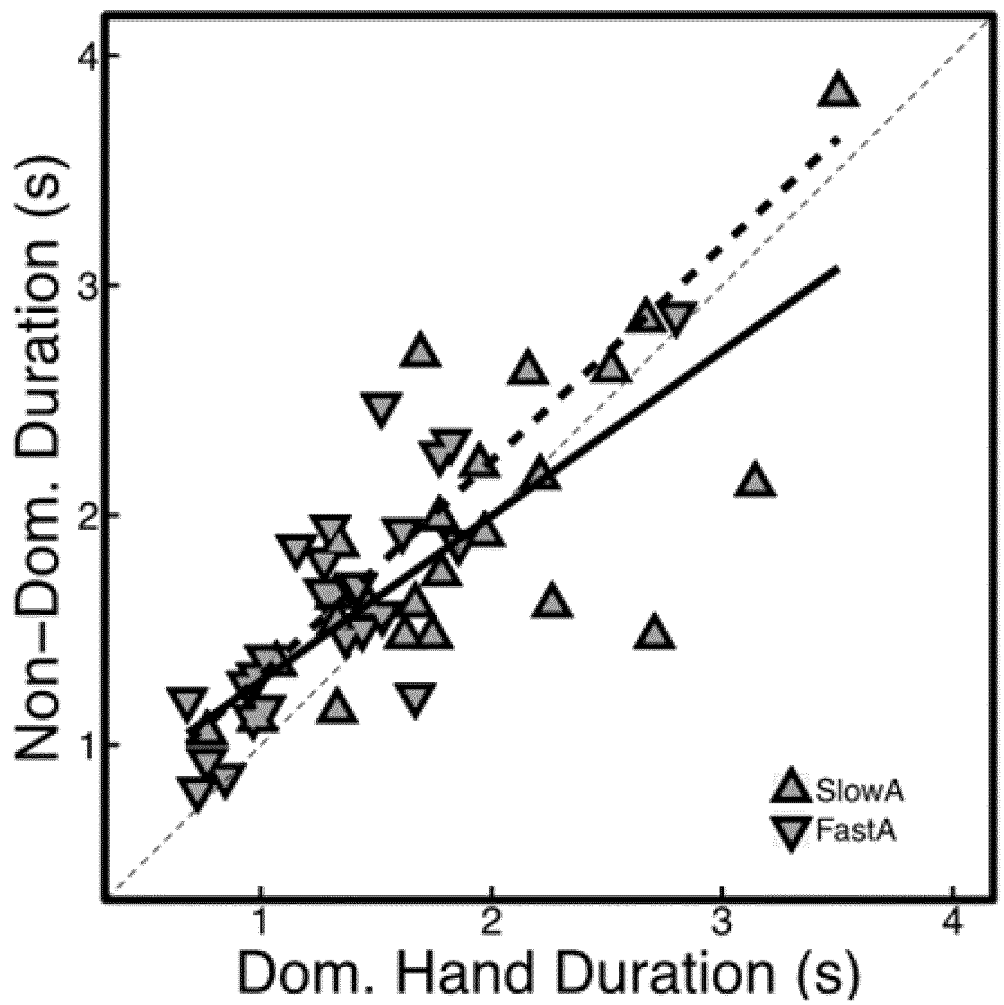
FIG. 7 is a graph illustrating the differences between the time taken to complete the TMT B test when using a dominant hand and a non-dominant hand.

The graph in FIG. 7 shows the results of a study with 82 healthy individuals of whom half performed the TMT with their dominant hand and half with their non-dominant hand. It was found that, as expected, non-dominant hand use (which interferes with executive processes) primarily affected executive processes. In FIG. 7, the median completion times for each element/target of the TMT B performed with the non-dominant hand are plotted against the median completion times for each element of the TMT B performed with the dominant hand. The subjects were evenly divided into two groups, those that performed the TMT quickly (FastA) and those that performed the TMT slowly (SlowA). A regression line was formed for each of the fast and slow groups, and thus the two lines are separate regression lines for subjects with a fast TMT A and a slow TMT A. This separation is made because non-dominant hand use only affected performance of the participants with a fast TMT A. The solid line 45 is the regression line for the fast group, and is formed as a least squares linear fit to the completion time data for the fast group. The dashed line 46 is the regression line for the slow group, and is formed as a least squares linear fit to the completion time data for the slow group. The thin dashed line 47 has a slope of 1 and indicates equal performance for the dominant hand and the non-dominant hand.

If non-dominant hand use primarily affected layout-related processes, the fitted regression lines 45, 46 would have a slope larger than 1 because completion times in the non-dominant hand condition would go up for elements that require more time to process. This is based on the notion that also with the dominant hand completion time increases for elements that have higher demands in terms of visual attentional and motor processing. If on the other hand non-dominant hand use mainly affected executive functions, the lines would shift upwards (i.e. be offset) relative to the dashed line but the slope would remain 1. This is based on the notion that all elements have similar completion times in terms of executive processing. As can be seen in FIG. 7, the data is mostly in line with the latter. Both the fast and slow TMT A groups have a slope smaller than 1.

However, in the left part of FIG. 7, the lines 45, 46 are above the dashed line 47 showing that the non-dominant hand condition was relatively slow on elements with short completion times, i.e. elements that have low visual search and motor demands. The results of this analysis show that the reduced performance with the non-dominant hand relative to the dominant hand is not due to visual attentional/motoric processes, but due to executive functions.

Using this FIG. 7, the two metrics are easy to understand. The slope of the fit (the regression line) relates to visual attentional/motoric processing, and the offset relates to executive functioning. In some embodiments, the offset is calculated at the average element completion time of the reference group (not at completion time=0).

A clinical evaluation of the subject on these two metrics can be done in relation to norm scores, based on a norm group of subjects, with the slope and offset of the subject's regression line being compared to the slope and offset of the norm group. Alternatively, these metrics could be related to variance in the data of the subjects in the reference group, for example standard deviation of the offset and the slope for the reference group. In the long term, norm scores need to be collected and an individual patient's performance should be compared to the slope and the offset of the norm group in order to determine the patient's visual attentional/motoric functioning and his executive functioning. However, up to that point the performance of the patient can be related to the variance in the reference group. To get an indication, a standard deviation on offset as well as slope could be calculated by bootstrapping the reference group data. By drawing participants multiple times (>1000×) at random from the reference group and determine his slope and offset of the regression line, a distribution can be built and a standard deviation calculated. With these parameters, the distance of the patient on the two new metrics to the population can be determined and expressed.

Figure 8:
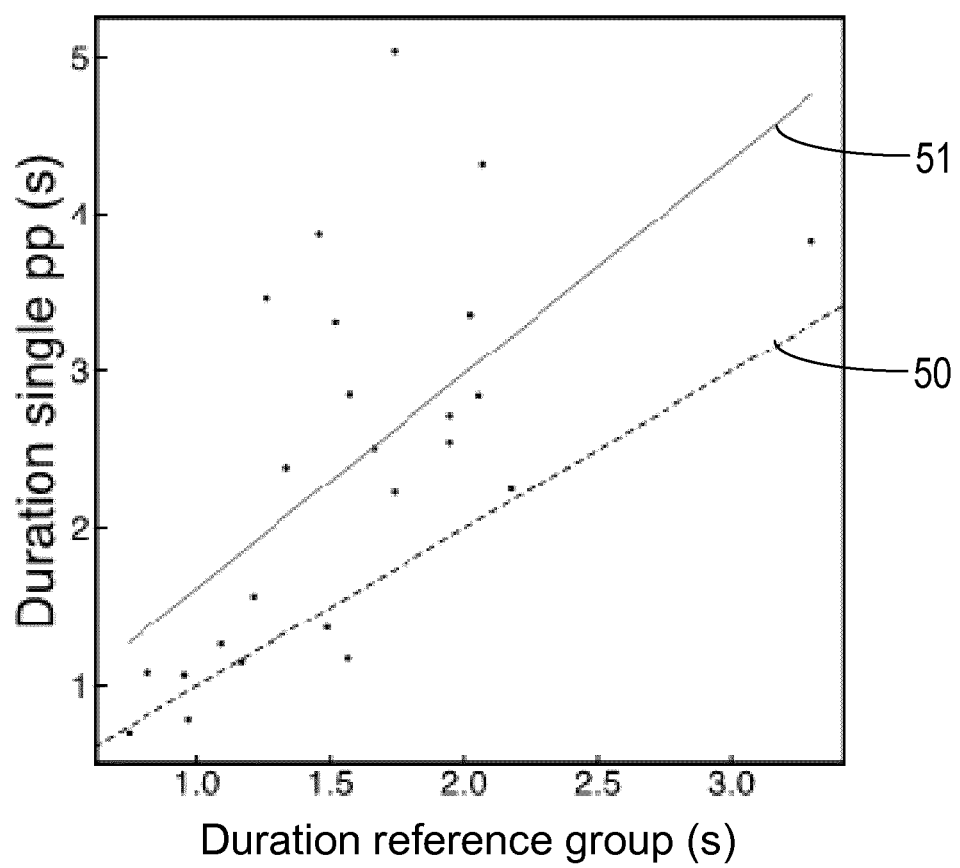
FIG. 8 is a graph illustrating the performance of a TMT test by a subject with an executive cognitive dysfunction relative to a reference group.
Figure 9:
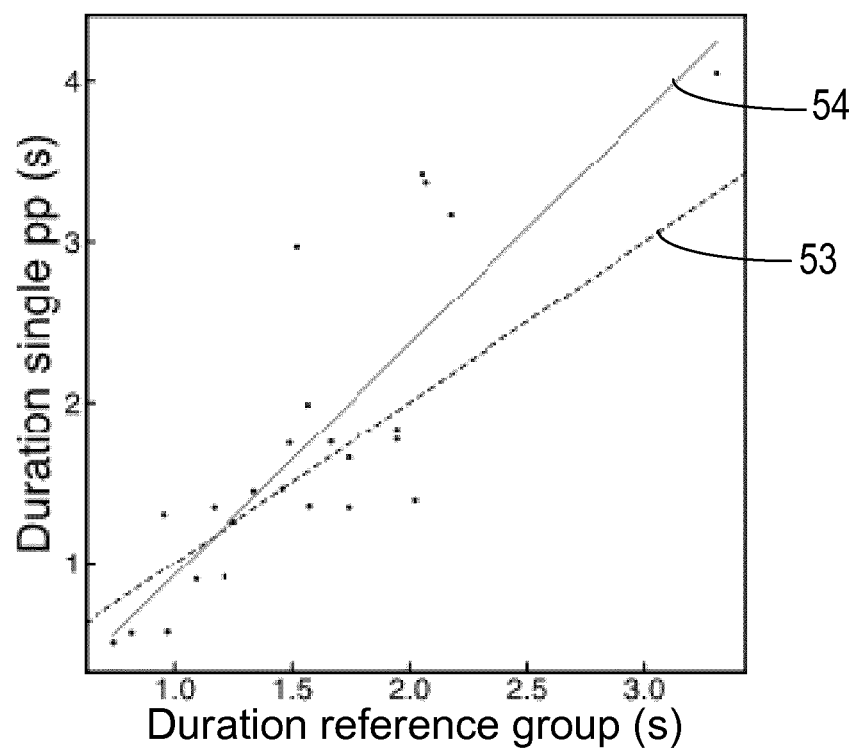
FIG. 9 is a graph illustrating the performance of a TMT test by a subject with a visual attention/motoric dysfunction relative to a reference group.

FIGS. 8 and 9 are graphs that show the regression lines for two subjects (single pp) relative to a reference group. A different approach is based on statistics; a decision can be made whether abnormal performance is related to executive functioning or to layout related processes. In particular, the regression line derived from the completion time data for two subjects is compared to data for a reference group in which the subjects in the reference group used their right hand (their dominant hand) for the test. FIG. 8 shows the completion time for each target/element for a subject plotted against the average (e.g. median) completion time for that target for the reference group. In this example, the subject is slow relative to the subjects in the reference group due to an executive cognitive process dysfunction. This can be seen in FIG. 8 by the data points being mostly positioned above the diagonal dashed line 50 (which has slope 1). Line 51 is a linear fit to the subject's data and shows that the subject's completion times are clearly offset relative to the reference group. Statistical analysis confirms that the subject's data is offset ($p<0.001$) but there is no statistical difference in slope ($p=0.327$).

In the example of FIG. 9, the subject has a slow performance due to layout-related processes. This subject is, on average, not slow and consequently there is no difference in offset relative to the reference group ($p=0.127$). However, the slope is significantly larger than a slope of 1 which indicates that the subject's layout-related processes are different from those of the reference group ($p=0.0422$).

Thus, this statistical approach provides the ability to identify subjects with significantly different layout-related processes while their overall performance may appear normal. This can occur when the subject has an above-average executive processing speed and uses this to compensate for visual problems. The above approach may give the neuropsychologist additional evidence for visual or motoric deficits identified in other test which was not possible without the current invention.

Measure of Literary Function

Another measure that could be derived from the completion time information for a subject provides an indication of the literary function of the subject. In particular the measure is based on comparing the time taken to complete number targets to the time taken to complete letter targets.

The interpretation of the results of TMT B relies on the assumption that the switch from letter to numbers and vice versa only introduces additional load on executive functions. However, this is not the case. In particular, the TMT B introduces the use of letters in addition to numbers whereas the TMT A only contains numbers. Therefore, in addition to increasing the load on executive functions, the TMT B also increases the load on language processing. Subjects who have reduced literacy skills may have slower completion times. Abnormally slow completion times on the TMT B (in relation to TMT A) may thus be falsely attributed to executive cognitive dysfunction.

Another version of the TMT, i.e. the DKEFS TMT, contains subtests to separately measure an individual's performance on a number-sequencing task and a letter-sequencing task in addition to the traditional switching-task. The number-sequencing task measures how fast an individual can connect only numbers, whereas the letter-sequencing-task measures how fast an individual can connect only letters. This can give an indication as to whether an individual is unexpectedly slow on one of these tasks which could then explain an abnormal score on the switching-task. The downside of the DKEFS approach is that it requires the subject to perform additional tests which requires additional time. Digital measurement of TMT B performance enables a separate measurement of letter cancellation and number cancellation without any additional tests.

In addition to the completion time data for the subject, a reference data set is required that contains completion time data or TMT B test results in another format (e.g. a video of the test or raw data from the data input element, such as a touchscreen) for a number of subjects. A data set is needed of healthy subjects that at least match the subject's age, education level, and/or handedness (i.e. which hand the subject writes with (also known as the dominant hand) and/or which hand was used for the test). Where the reference data is not provided in the form of completion times, the data will need to be processed to calculate element completion times.

The total and/or average completion time for the subject is calculated separately for all number targets and all letter targets, resulting in two total and/or average completion times. The time taken to complete a particular target is the time from the completion of the preceding target to the completion of that target. The time at which a target is completed can be the time at which the subject-specified path crosses the boundary of the target, or it can be the time at which the subject starts to 'dwell' on a target (which can be determined as the time that the velocity of the path generation (e.g. the velocity of the pen or stylus) falls below a threshold value). In the latter case, it can be assumed that processing (particularly visual) of the next target by the subject starts as soon as the pen/stylus starts to 'dwell' on the previous target. Assuming that the switch costs are similar for switching from a letter to a number as from a number to a letter, if the total completion time for the cancellation of the letters is significantly higher (either compared to the total completion time for the cancellation of the numbers or compared to a reference group), it may be concluded that the individual's increased total completion time may be due to problems processing letters rather than to a deficit in executive functions. The difference in the letter completion time and the number completion time can also be determined, and/or the ratio of the letter completion time to the number completion time. These measures may provide indications of letter abilities relative to number abilities.

Similar total and/or average measures, and/or the difference and ratio can be calculated for the reference population.

The measures for the subject can then be compared to the measures for the reference population. For example the measures for the subject can be compared to norm data, or compared to an estimate of the population distribution. The subject's performance could be expressed in the form of a variance parameter, for example the number of standard deviations away from the average.

Figure 10:
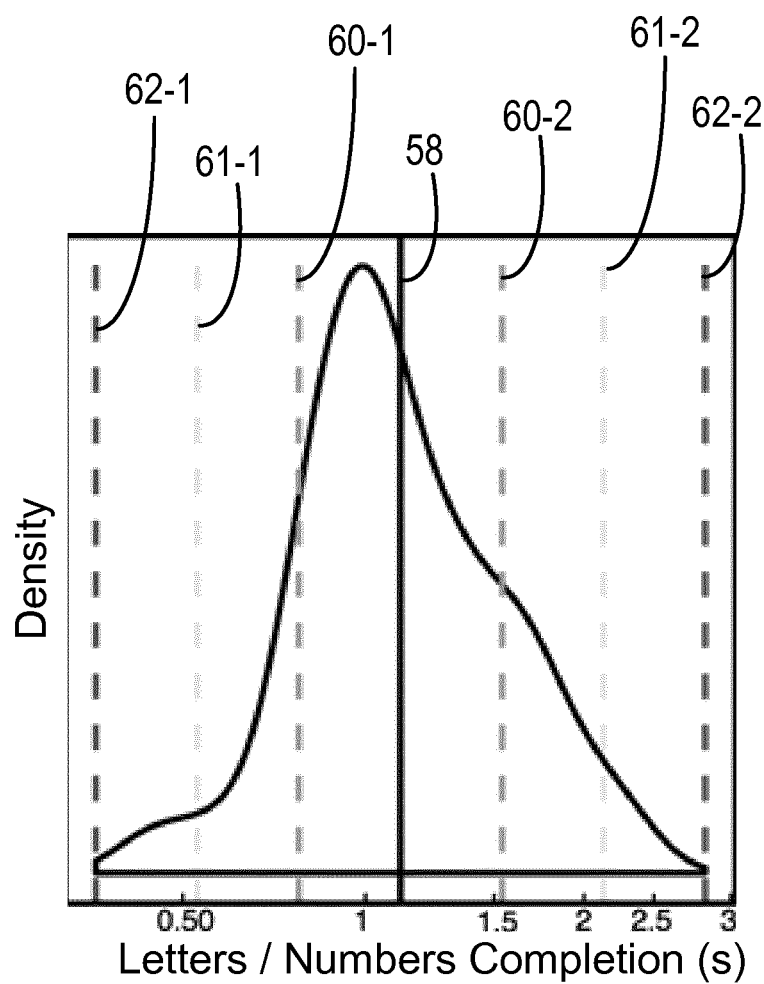
FIG. 10 is a graph plotting the ratio of the letter completion time to the number completion time for a reference population.

The graph in FIG. 10 plots the ratio of the letter completion time to the number completion time for a reference population. As can be seen, the average ratio (shown by line 58) is slightly higher than 1 meaning that on average subjects are slower at processing letters than numbers. The mode is around 1 meaning that for the majority of the subjects there was no difference in processing time. This data is for 41 participants who completed the TMT B with their dominant hand. The dashed lines indicate 1 (lines 60-1, 60-2), 2 (lines 61-1, 61-2) and 3 (lines 62-1, 62-2) times the standard deviation away from the average.

The output measure can be based on a comparison of the letter/number completion time ratio to the standard deviation measures, with the output measure indicating an abnormal result (i.e. literary dysfunction) if the letter/number completion time ratio deviates more than, for example, 3 times the standard deviation from the average.

With the output measure described above, an assessment of executive cognitive functioning can be made free of any literacy biases. This can be done by comparing the number-only completion time on the TMT B with the total completion time on the TMT A. Again, norm scores can be determined for the ratio between numbers-only TMT B completion times and TMT A completion times, or any other score or an estimate of the population distribution for such a measure can be determined.

Various exemplary statements relating to embodiments and aspects of the invention are set out below:

1. A computer-implemented method for determining an indication of visual attention/motoric dysfunction, and ii) an indication of executive cognitive dysfunction of an individual during or following a digital test comprising a plurality of targets, the method comprising the steps of:
   receiving element data from a database;
   determining a parameter (e.g. time) taken by the user between a first and a second target of the plurality of targets, wherein the first and second targets are consecutive targets of different cognitive aim in accordance with the test protocol;
   identifying from the element data the data corresponding to the first and the second target;
   comparing the determined parameter based on the identified element data by means of a mathematical normalizing formula, such as linear regression; and
   outputting information based on said comparison of i) an indication of visual attention/motoric dysfunction, and ii) an indication of executive cognitive dysfunction.

2. A computer-implemented method for determining an inter-variability value of an individual during or following a digital test comprising a plurality of targets, the method comprising the steps of:
   receiving inter-variability data from a database;
   determining a parameter (e.g. time) taken by the user between a first and a second target of the plurality of targets, wherein the first and second targets are consecutive targets in accordance with the test protocol;
   associating the inter-variability data with the determined parameter;
   normalizing the determined parameter based on the associated inter-variability data by means of a mathematical normalizing formula; and
   calculating the inter-variability value based on the normalized determined parameter.

3. The method of statement 2, further comprising the step is to identify abnormal inter-variability value for a given user based on the inter-variability data.

4. A system for determining an indication of visual attention/motoric dysfunction, and ii) an indication of executive cognitive dysfunction of an individual during or following a digital test comprising a plurality of targets, the system comprising:
   Storage means having element data from a database;
   A processor configured to determine a parameter taken by a user between a first and a second target of the plurality of targets, wherein the first and second targets are consecutive targets of different cognitive aim in accordance with a test protocol;
   identify from the element data the data corresponding to the first and the second target; and
   compare the determined parameter based on the identified element data by means
   of a mathematical normalizing formula, such as linear regression; and a display for outputting information based on said comparison of i) an indication of visual attention/motoric dysfunction, and ii) an indication of executive cognitive dysfunction.

5. The system according to statement 4 wherein the digital test is performed using a device for tracking movements of a user over a user interface, such as a pressure sensitive tablet and a digital stylus or camera.

6. The system according to statement 5 wherein the tablet further comprises a wireless transceiver for transmitting data to a host computer.

Appendix

Introduction

The Trail Making Test (TMT) is a frequently used neuropsychological test to assess aspects of attention and executive functions (Bowie & Harvey, 2006; Lezak, Howieson, & Loring, 2004; Tombaugh, 2004; Wagner, Helmrich, Dahmen, Lieb, & Tadic, 2011). The TMT consists of two parts. Part A involves making a trail between the numbers in ascending order. Part B consists of 13 numbers and 12 letters which the patient is instructed to connect in an alternating pattern. The patient is asked to complete the trails as quickly as possible and completion time is measured as main outcome (Bowie & Harvey, 2006; Lezak et al., 2004). Clinical interpretation of performance on the TMT is based on part A mainly reflecting visual search and motor speed skills and part B also requiring higher cognitive functions such as cognitive flexibility, task switching and working memory (Lezak et al., 2004). Since part B is a more complex task, completion time is longer for part B than part A and the B-A difference as well as the B/A ratio are considered to reveal deficits in executive functions (Arbuthnott & Frank, 2000; Bowie & Harvey, 2006; Corrigan & Hinkeldey, 1987; Gaudino, Geisler, & Squires, 1995; Kortte, Horner, & Windham, 2002; Lezak et al., 2004; Reitan & Wolfson, 1995; Yochim, Baldo, Nelson, & Delis, 2007).

Several factors are known to affect TMT completion time. Research has consistently shown that performance on the TMT is strongly influenced by age and education with completion time on both parts of the TMT increasing with growing age and fewer years of education (Amodio et al., 2002; Fromm-Auch & Yeudall, 1983; Robins Wahlin, Backman, Wahlin, & Winblad, 1996; Salthouse & Fristoe, 1995; Tombaugh, 2004). Age was found to have a larger effect on completion time than education and the effect of both age and education was found to be more pronounced on part B than on part A (Tombaugh, 2004). The effect of age on TMT performance was found to be independent of age-related motoric or sensory limitations and seems to be mainly due to a general decline in cognitive functioning (Robins Wahlin et al., 1996; Salthouse & Fristoe, 1995). Two other factors that have been investigated are handedness and dominant versus non-dominant hand use. Due to the layout of the TMT, when performing the test with the left hand, different elements are obstructed by the hand than when performing the test with the right hand which may cause intermanual differences in completion time. Aside from the layout, it has been suggested that left-handed individuals outperform right-handed individuals on executive tasks possibly because of greater interhemispheric communication in left-handed people (Beratis, Rabavilas, Kyprianou, Papadimitriou, & Papageorgiou, 2013; Gunstad, Spitznagel, Luyster, Cohen, & Paul, 2007; Polich & Hoffman, 1998). This notion is supported by studies that found an intermanual difference in total completion time in favor of left-handed people on TMT B but not TMT A (Beratis et al., 2013; Gunstad et al., 2007).

Besides handedness, another factor that may influence TMT performance in a clinical setting is the use of the non-dominant hand. This is an important factor since patients who suffer from partial paralysis or other motor dysfunction that prevent them from using their dominant hand may be required to perform the TMT with their non-dominant hand. Currently, no norm scores are available for the completion time of the TMT with the non-dominant hand which makes it difficult to interpret completion times and derived scores like the B-A difference and the B/A ratio. An increase in completion time or derived score may be falsely attributed to non-dominant hand use which may result in an underestimation of cognitive problems; alternatively, an increase in completion time or derived scores may be falsely attributed to a cognitive problem rather than hand use which would result in an overestimation of cognitive problems.

Performance may be assumed to be better for the dominant hand and to decrease for the non-dominant hand as the task complexity increases. Research has shown that generally, performance on a motor task is slower for the non-dominant hand which is assumed to be mainly attributable to lower movement accuracy and a larger need for corrective movements with the non-dominant hand (Annett, Annett, Hudson, & Turner, 1979). Research has furthermore shown that healthy individuals are markedly slower when performing a standard neuropsychological test involving fine motor skills such as copying or cancellation (Cramond, Clark, & Smith, 1989) or name-writing (Fromm-Auch & Yeudall, 1983) with the non-dominant hand.

Aside from limited motor performance, there is evidence for an interference effect between simultaneous performance of a motor and a cognitive task in general. Several studies have employed a dual task paradigm to study the interaction between the performance of a motor task such as walking and the simultaneous performance of a cognitive task. These studies have consistently shown that simultaneously performing a motor and a cognitive task increases cognitive load and results in an interference effect with performance on both tasks deteriorating (Baddeley & Della Salla, 1996; Hausdorff, Yogev, Springer, Simon, & Giladi, 2005; Lindenberger, Marsiske, & Baltes, 2000; Siu, Chou, Mayr, van Donkelaar, & Woollacott, 2008; Theill, Martin, Schumacher, Bridenbaugh, & Kressig, 2012).

When looking at hand use specifically, there is evidence that suggests non-dominant hand use may consume additional cognitive resources and therefore interfere with the performance of a cognitive task. Healthy individuals were found to perform the recall part of the Rey Osterrieth Complex Figure Test significantly worse when they had used their non-dominant hand as opposed to their dominant hand when copying the figure (Yamashita, 2010). According to the author, this finding is due to drawing the figure with the non-dominant hand constituting a dual task which leads to fewer cognitive resources being allocated to the performance of the cognitive task, i.e. the copying of the figure. This interpretation is supported by a study that found slowed performance on a cognitive test that requires executive function, i.e. random number generation, when participants simultaneously performed a motor speed task, i.e. the Grooved Pegboard task, with their non-dominant hand. This dual-task interference effect was not found for the dominant hand (Strenge & Niederberger, 2008).

Insights from imaging research support the notion that using the non-dominant hand to perform a motor task while simultaneously performing a cognitive task compromises the performance on both tasks since they draw on similar cognitive resources. Research has shown that performing a simple motor task (sequential finger movements) with the non-dominant hand results in greater cortical activity than performing a simple motor task with the dominant hand and in similar cortical activity as performing a complex motor task (random finger movements) with the dominant hand (Mattay et al., 1998). Similarly, another study (Jancke et al., 1998) has shown that performing a sequential movement with the non-dominant hand (in right-handed subjects) results in greater right hemisphere activation compared to the left hemisphere activation during performance of the same movement with the dominant (right) hand. These findings suggest that motor movements with the non-dominant hand are less familiar and automatic and therefore consume more cognitive resources than movements with the dominant hand.

Taken together, these findings suggest that performing a motor task with the non-dominant hand while simultaneously performing a cognitive task increases cognitive load which compromises performance on both or one of the two tasks. We believe that performing the TMT A with the non-dominant hand will not or only marginally slow down completion time since there is less competition for the same cognitive resources because the TMT A mainly reflects visual search and motor speed skills and does not rely on higher order cognitive functions. Furthermore, performing the TMT B with the non-dominant hand increases completion time since performance of the TMT B requires higher order cognitive functions besides visual search and motor speed skills and therefore both the TMT B and use of the non-dominant hand will compete for the same limited cognitive resources.

To our knowledge, three studies have explored the effect of dominant versus non-dominant hand use on completion time of the TMT (LoSasso, Rapport, Axelrod, & Reeder, 1999; Toyokura, Sawatari, Nishimura, & Ishida, 2003a; Toyokura, Ishida, Watanabe, Okada, & Yamazaki, 2003b). LoSasso and colleagues (1999) have compared the completion time of the original TMT as well as a parallel version of the TMT for 40 right-handed and 40 left-handed individuals who performed both tests with their dominant and their non-dominant hand. Completion time was found to be slightly longer for the non-dominant hand for both the original and the parallel TMT B. This intermanual difference was however not significant and considered clinically irrelevant (LoSasso et al., 1998). Toyokura and colleagues (2003a, 2003b) have explored differences in completion time for the Japanese version of the TMT which consists of numbers (part A) and numbers and Japanese kana letters (part B). Their first study included a total of 150 healthy participants of whom 50 completed the Japanese TMT with their dominant hand, 50 with their non-dominant hand and 50 completed a mirrored version of the Japanese TMT with their non-dominant hand (Toyokura et al., 2003a). Completion times did not significantly differ for any of the three groups (Toyokura et al., 2003a). In the second study, 44 healthy volunteers were instructed to complete the Japanese TMT with their dominant and their non-dominant hand and to complete a mirrored version with their non-dominant hand. The sequence of these tasks was counterbalanced and they took place with an interval of four weeks between each task. In line with their first study, no intermanual difference in completion time was found (Toyokura et al., 2003b).

Although these three studies provide interesting insights into TMT performance with the dominant and non-dominant hand, there are a number of important limitations which make it difficult to conclude at this time that there is no clinically relevant difference between performing the TMT with the dominant or non-dominant hand. First, completion time was measured manually with a stopwatch in all three studies. Manual measurement of completion time may not always be precise which may introduce significant variance unrelated to the participants in these studies. Second, the exact administration procedure of the TMT is not explained in any of the three studies and it is therefore unclear what the begin and end times of the measurement were and to what degree errors affected completion time. Differences in administration account for the large variability in TMT completion times reported in different studies which is problematic and considered to be an important limitation of the TMT (Soukup, Ingram, Grady, & Schiess, 1998; Woods, Wyma, Herron, & Yund, 2015). In particular, errors on the TMT that are pointed out by the examiner and then corrected by the individual are problematic since they reflect examiner timing and have a substantial impact on total completion time. Additionally, self-correction of an erroneous movement can substantially increase the total completion time. It is unclear how many subjects made an error on the TMT in the three studies described above and whether these individuals were included in the analyses.

An important limitation of the Toyokura et al. studies (2003a, 2003b) is that the Japanese version of the TMT was used which is not directly comparable to the original TMT. The mean completion time for part A of the Japanese TMT was 70.1 seconds and for part B 83.3 seconds for a sample with a mean age of 26 years when completing the TMT with the dominant hand (Toyokura et al., 2003a). The ratio between the TMT A and the TMT B is much higher for the original version of the TMT indicating that part B is more difficult than part A (Tombaugh, 2004). Given that the B/A ratio is very small for the Japanese TMT it seems that there is a difference in task switching costs between the original and the Japanese TMT which makes it impossible to draw any valid conclusions about intermanual differences in completion time for the original TMT based on the Toyokura et al. studies (2003a, 2003b).

Our research explored the differences in dominant and non-dominant hand use on the TMT in a sample of healthy individuals in a large age range. More specifically, we tested whether non-dominant hand use increases completion time on the TMT B and less or not at all on the TMT A. As a consequence, we expect clinically relevant measures such as the B/A ratio to be affected by hand use. We assumed that non-dominant hand use requires cognitive resources which will interfere with performance of TMT B because it requires more higher order cognitive resources than the TMT A which mainly reflects visual search and motor speed skills. TMT performance was recorded digitally to overcome some of the shortcomings of previous research (LoSasso et al., 1998; Toyokura et al., 2003a, 2003b) and to be able to explore other measures in addition to total completion time.

Method

Participants 117 healthy right-handed individuals participated in the study. Handedness was determined with the Edinburgh Handedness Inventory. One participant was found to have a tendency for left handedness (score of −0.48) and he was therefore excluded from further analyses. Data of eleven participants were not included because of technical issues. Of the remaining 105 subjects, 23 (21.9%) had made a mistake during either the TMT A or the TMT B or both and were therefore excluded from further analyses. Participants who had made a mistake were excluded to obtain a pure measure of total completion time since as described above correction of errors has a substantial impact on total completion time. A mistake was defined as any path that deviates from the correct path, e.g. if a subject went from 18 to 20 rather than from 18 to 19. The number of participants who had made a mistake was similar for both conditions (ten in the dominant hand condition and 13 in the non-dominant hand condition (see below for a description of the conditions). The remaining 82 participants (28 women, 54 men) were all right-handed as measured with the Edinburgh Handedness Inventory (M=0.8, SD=0.15). They ranged in age from 20 to 65 years (M=36 years, SD=12 years). 57 participants (69.5%) had a University degree ranging from a BSc to a PhD. All participants had normal or corrected-to-normal vision and were employed at Philips Research.

Materials

Movements of the participants were recorded with a Wacom Intuos Pro tablet and Intuos inking pen. The pen writes on paper and registers movements on the tablet. The tablet was placed underneath the paper version of the TMT. Every new sheet of paper was aligned to markers on the tablet to assure that all TMT's were performed at the exact same location on the tablet. The position of the paper was fixed by taping it to the tablet.

A digital tablet, such as the Wacom® Intuos® Pro tablet, sampled the pen position at 133 Hz. Pen positions were recorded with Movalyzer (developed by Neuroscript). Pen pressure was not calibrated and therefore not used in the analyses.

Additional Digital Parameters for the TMT

Completion times were determined from the raw pen position data. They were calculated as the difference in time between the moment the pen touched the tablet at the first element and the moment the pen stopped at the last element of the TMT. The pen stop was defined as the velocity of the pen dropping below threshold velocity within 1 cm of the center of the last element. Velocity was calculated as the instantaneous velocity using a second order polynomial fit to interpolate within a window of five samples centered on the sample of interest. Threshold velocity was adaptively determined through an iterative process for each individual TMT trial to account for noise in the tablet as well as human motor noise. First, a threshold was set arbitrarily. Next, a new threshold was calculated as five times the standard deviation above the mean of the velocity of all samples below the predefined threshold. If the resulting value was lower than the predefined threshold, it was set as the new threshold and a new iteration of the same procedure was executed. This was repeated until the newly calculate threshold was identical to the previous one. Aside from total completion time, we also performed more detailed analyses of the trails. For this purpose, we fully automatically detected the order in which the elements in the TMTs were completed and extracted features per completion. Automatic detection of completion paths was conducted by comparing the spatial pattern within the area closest to an element (or Voronoi cell) with two simple model patterns. One of those model patterns represented completion of the element by connecting the element with the pen entry and exit of the Voronoi cell with two lines (one from the entry into the Voronoi cell to the element and one from the element to the point of exit out of the Voronoi cell); the other model represented no completion with a single line connecting entry and exit of the area. The decision whether an element was completed or not was made based on the similarity of the data to the two models (using a 2D least squares method).

If both models made similar predictions (e.g. when an element was completed in a straight path), the decision was made based on whether there had been a local drop in pen velocity close to the element (within a radius of 0.5 cm of the center of the elements). All classifications (whether an element was completed or not) were then inspected manually; only eight of a total of 4100 (i.e. 82 times 25 TMT As+82 times 25 TMT Bs) classifications were incorrect and had to be corrected manually.

An important aspect of TMT performance we were interested in was the time needed to move from one element to the next (element completion time). This was defined as the total time required for finding, planning, processing and executing the movement to the next element. The assumption is that this starts as soon as the preceding element is completed and ends when the target element is completed. We define the moment of completion as the moment the pen starts to move with subthreshold velocity as it is approaching the target element. Velocity threshold was calculated in the same way as mentioned above.

Results

There were no differences in age (t(80)=−0.365, p=0.716), handedness (t(80)=−0.603, p=0.548), gender ($X^2$ (1, N=82)=0.868, p=0.352) and education level ($X^2$ (1, N=82)=1.439, p=0.230) between the two conditions. The mean completion time for TMT A was 30.55 (SD=8.59) seconds measured with the stopwatch and 26.41 (SD=7.00) seconds measured digitally. This difference is statistically significant (t(81)=−10.89, p=0.000). The mean completion time for the TMT B was 52.82 (SD=13.22) seconds measured with the stopwatch and 48.61 (SD=12.46) seconds measured digitally which is also a statistically significant difference (t(81)=−8.859, p=0.000).

Figure 11:
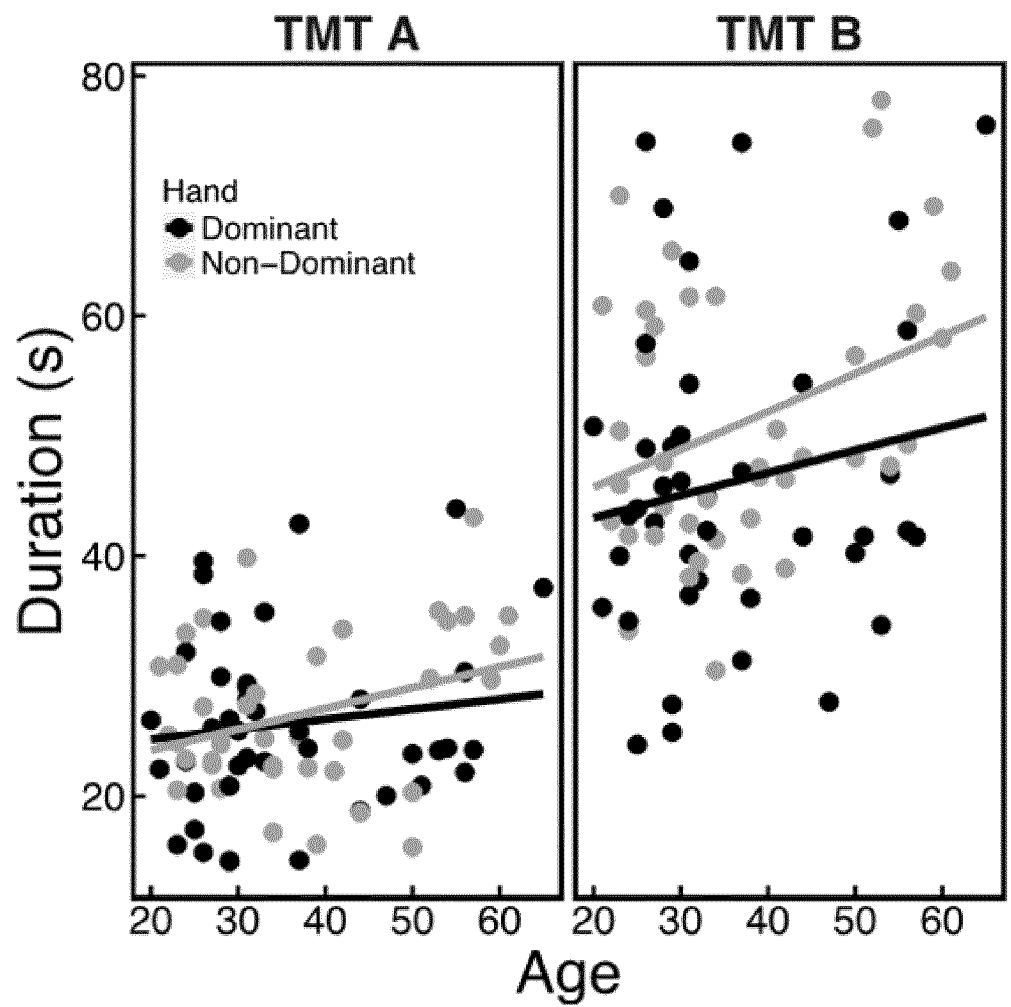
FIG. 11 shows completion times on TMT A and TMT B as a function of age.

In line with previous research (e.g., Tombaugh, 2004), age was found to correlate with both TMT A (r=0.223, p=0.044) and TMT B completion times (r=0.251, p=0.023) with completion times increasing with increasing age (see FIG. 11, which shows completion times on TMT A (left panel) and TMT B (right panel) as a function of age). In FIG. 11 each dot represents the completion time of one participant, black dots for participants in the dominant hand condition, yellow (grey) dots for participants in the non-dominant hand condition. The lines are regression lines. Neither education nor gender correlated with TMT A (education: $r_{pb}$=−0.158, p=0.157; gender: $r_{pb}$=0.01, p=0.926) or TMT B completion times (education: $r_{pb}$=0.021, p=0.853; gender: $r_{pb}$=−0.104, p=0.351).

The effect of Hand Use on TMT A and TMT B Completion Time

Figure 12:
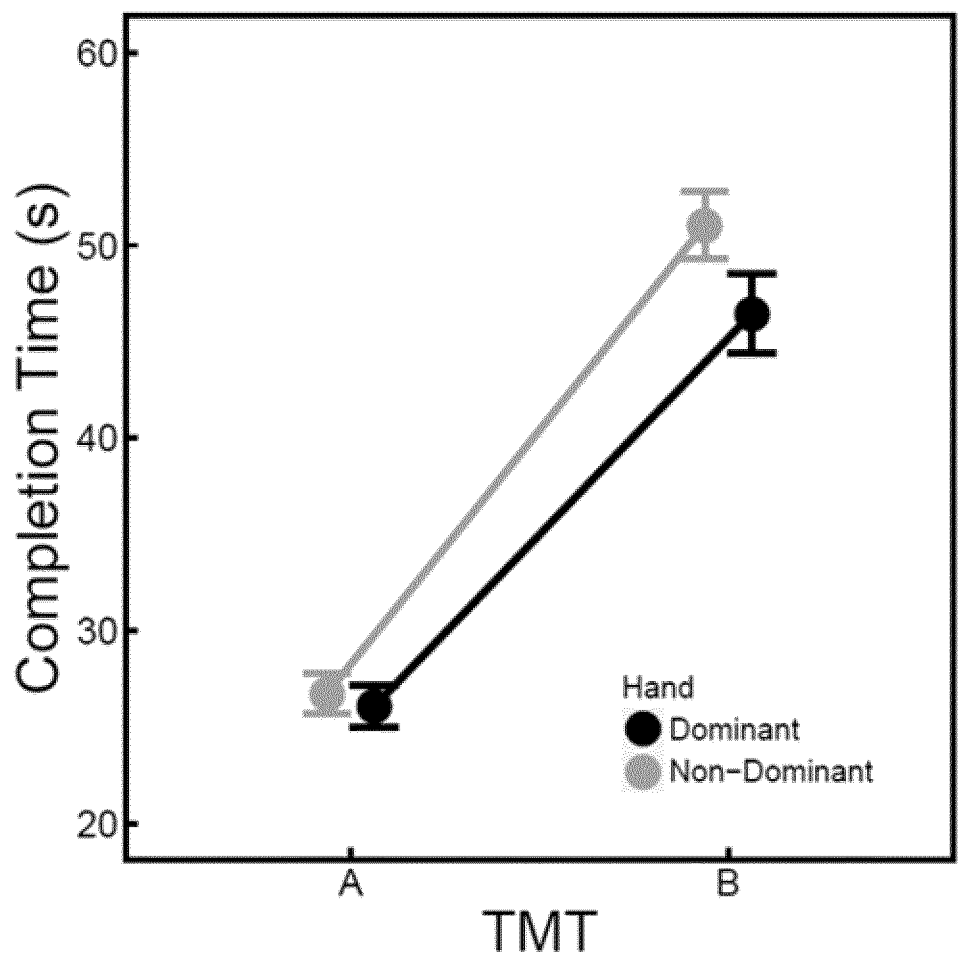
FIG. 12 shows the mean completion time for TMT A and B for the dominant and non-dominant hand condition.

As can be seen in FIG. 12, which shows the mean completion time for TMT A and B for the dominant (black dots) and non-dominant hand (yellow/grey dots) condition (where the error bars indicate the standard error of the mean), the mean completion time for TMT A is 26.06 (SD=7.33) seconds for the dominant hand condition and 26.76 (SD=6.73) seconds for the non-dominant hand condition. The mean completion time for TMT B is 46.17 (SD=13.21) seconds for the dominant hand condition and 51.05 (SD=11.28) seconds for the non-dominant hand condition. The difference between the dominant and non-dominant hand condition in completion time on TMT B is on average 4.88 seconds which is considerably higher than a difference of 1.9 seconds found in previous research (LoSasso et al., 1998). As described in the method section, TMTs that contained mistakes were not included in the analyses.

Figure 13:
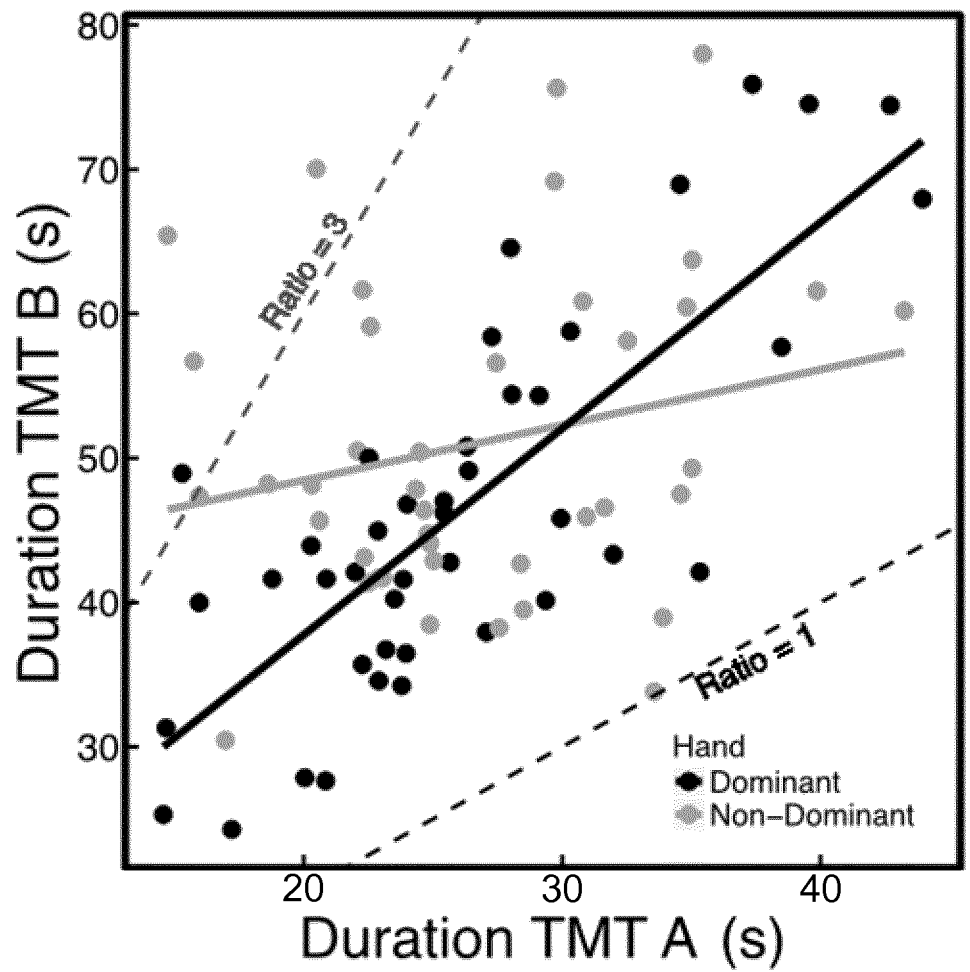
FIG. 13 shows the correlation between TMT A and B completion time for the dominant and non-dominant hand condition.

As expected, a General Linear Model (GLM) with age as covariate and condition as fixed factor revealed a main effect of age ($p=0.047$) and no difference between conditions in completion time for TMT A ($F(1, 79)=0.141$, $p=0.708$). A GLM including TMT B completion time as dependent variable, age and TMT A as covariates and condition as fixed factor revealed an interaction effect of condition and TMT A ($p=0.001$). As can be seen in FIG. 13, TMT A completion time is a good predictor for TMT B completion time in the dominant hand condition (correlation: $r=0.79$, $p=0.000$; slope: $\beta=1.42$) but not in the non-dominant hand (correlation: $r=0.229$, $p=0.15$; slope: $\beta=0.38$). Given the significant interaction effect of condition and TMT A in the model, TMT A completion time and condition were mean centered for better interpretability of the model. The GLM revealed a main effect of TMT A completion time ($p=0.000$), a trend for age ($p=0.068$) and a trend for condition ($F(1, 77)=3.757$, $p=0.056$). As can also be seen in FIG. 13, several participants have a B/A ratio score close to or above 3 which is considered a cut-off score for set-switching impairment in clinical practice (Arbuthnott & Frank, 2000). Of the ten participants with the highest B/A ratio score (all >2.5), eight were in the non-dominant hand condition and two were in the dominant hand condition. FIG. 13 shows the correlation between TMT A and B completion time for the dominant (black) and non-dominant hand (yellow/grey) condition. The dots indicate individual completion times, black dots for participants in the dominant hand condition, yellow/grey dots for participants in the non-dominant hand condition. The solid lines are regression lines. The red/grey dotted line (labelled "Ratio=3") indicates a B/A ratio of 3, the black dotted line (labelled "Ratio=1") indicates a B/A ratio of 1.

Figure 14:
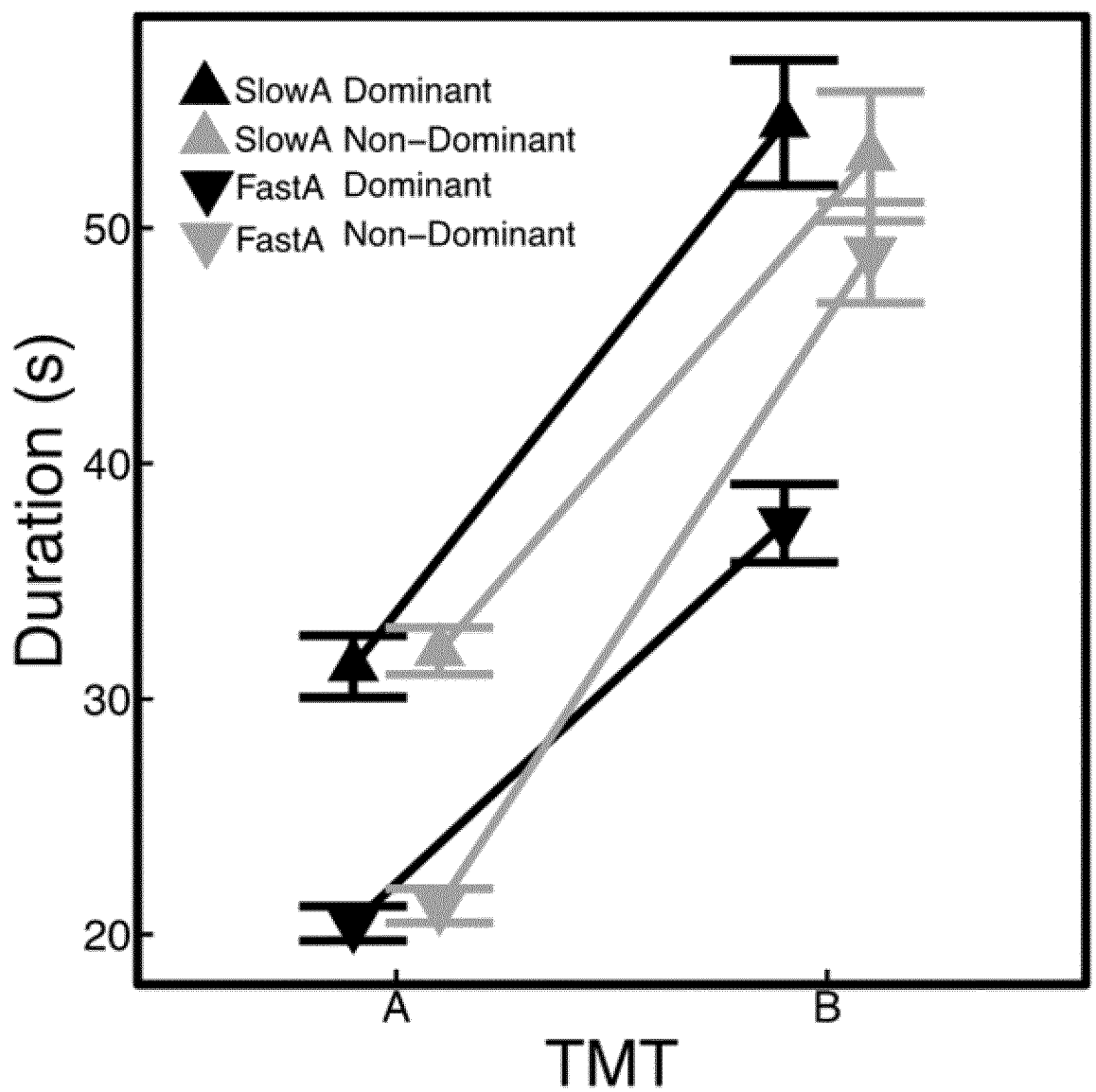
FIG. 14 shows the average completion times for TMT A and B after applying a median split on the TMT A.

We reanalyzed the data after distributing the participants in a slow TMT A group and a fast TMT A group based on a median split in order to better understand the interaction effect of condition and TMT A. As can be seen in FIG. 14, which shows the average completion times for TMT A and B after applying a median split on the TMT A (vertex up means slow TMT A, vertex down means fast TMT A), there is a significant difference between dominant and non-dominant hand condition on TMT B completion time for participants who had a fast completion time on TMT A ($t(39)=-4.125$, $p=0.000$) but not for participants who had a slow completion time on TMT A ($t(39)=0.461$, $p=0.648$). In FIG. 14, black lines and symbols represent the dominant hand condition, yellow/grey lines and symbols the non-dominant hand condition. The error bars are standard errors of the mean. This difference cannot be explained by demographic factors as there was no difference in age ($t(39)=0.738$, $p=0.465$), handedness ($t(39)=1.226$, $p=0.227$) and gender ($X^2 (1, N=41)=0.01$, $p=0.92$) between the fast and slow TMT A groups in the dominant hand condition and there was also no difference in age ($t(39)=-1.396$, $p=0.172$), handedness ($t(39)=-0.273$, $p=0.786$), gender ($X^2 (1, N=41)=1.336$, $p=0.248$) and education level ($X^2 (1, N=41)=0.042$, $p=0.837$) between the fast and slow TMT A groups in the non-dominant hand condition. In the dominant hand condition, there was a difference in education level ($X^2 (1, N=41)=5.159$, $p=0.023$) between the fast and the slow TMT A group with a larger proportion of subjects with a higher education in the fast TMT A group, but it seems unlikely that this explains the difference in completion time on TMT B.

In the fast TMT A group, the difference between dominant and non-dominant hand condition in completion time on TMT B is on average 11.04 seconds which is considerably higher than a difference of 1.9 seconds found in previous research (LoSasso et al., 1998).

TMT B/A Ratio

Figure 15:
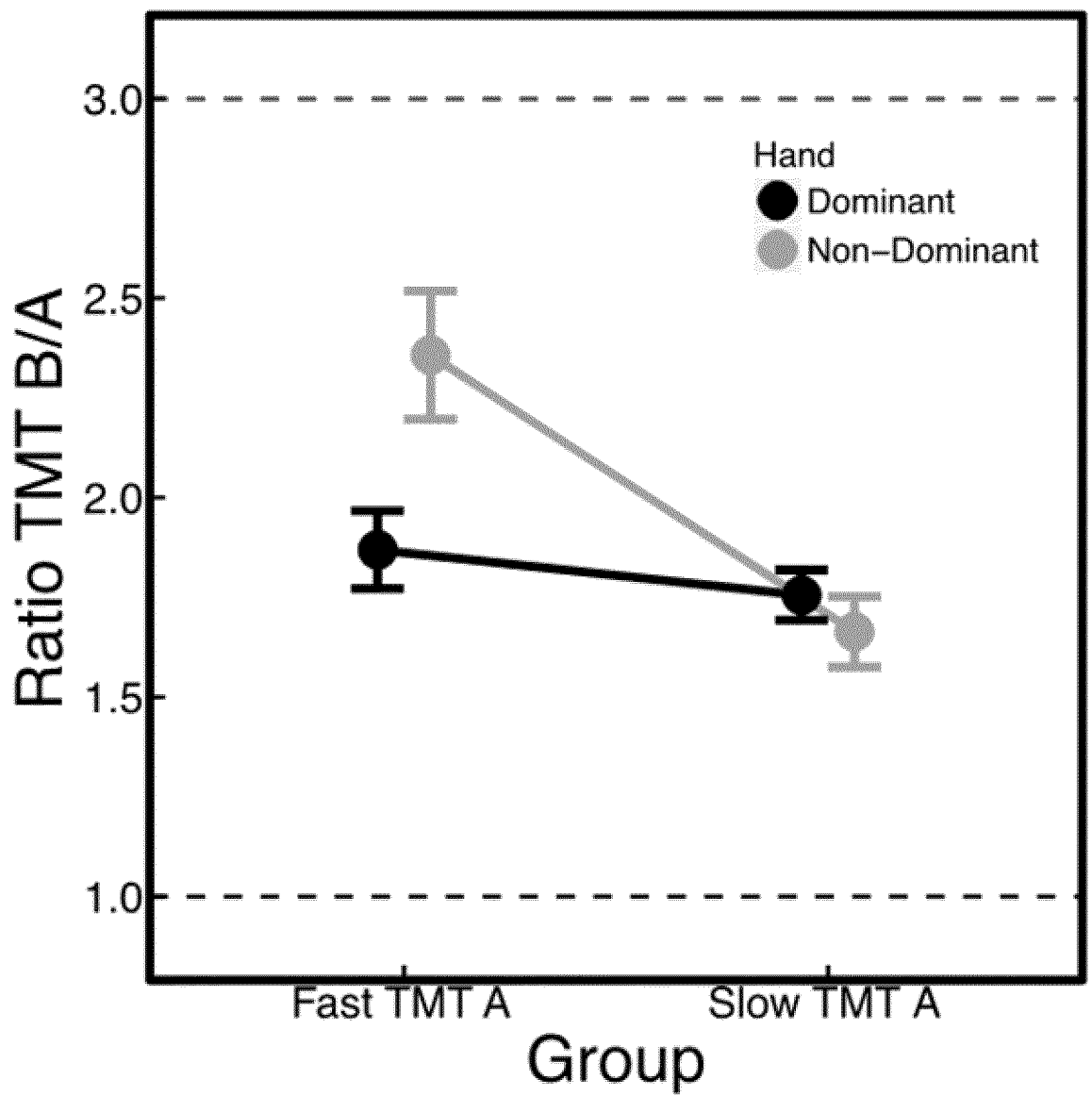
FIG. 15 shows the mean B/A ratios for the fast and slow TMT A groups in the dominant and non-dominant hand condition.

TMT B completion times for participants who performed the TMT A fast with their non-dominant hand were markedly different from the other groups. Is this also reflected in the clinically relevant B/A ratio? The mean B/A ratio score for the dominant hand condition is 1.8 (SD=0.38) compared to 2.02 (SD=0.68) in the non-dominant hand condition. A two-tailed independent t-test shows this difference is not statistically significant ($t(80)=-1.758$, $p=0.084$). When dividing the sample into a fast TMT A and a slow TMT A group based on the median split, the difference between the dominant and non-dominant hand condition on the B/A ratio score is significant in the fast TMT A group ($t(39)=-2.717$, $p=0.01$), but not in the slow TMT A group ($t(39)=0.635$, $p=0.529$) (see FIG. 15). FIG. 15 shows the mean B/A ratios for the fast and slow TMT A groups in the dominant (black dots) and non-dominant hand (yellow/grey dots) condition. The error bars are standard errors of the mean. The red/grey dashed line (upper line at ratio=3.0) indicates a B/A ratio of 3. The black dashed line (lower line at ratio=1.0) indicates a B/A ratio of 1 which means no additional time cost for switching sets on the TMT B relative to the TMT A.

Segment-by-Segment and Element-by-Element Analysis of TMT Completion Times

Figure 16:
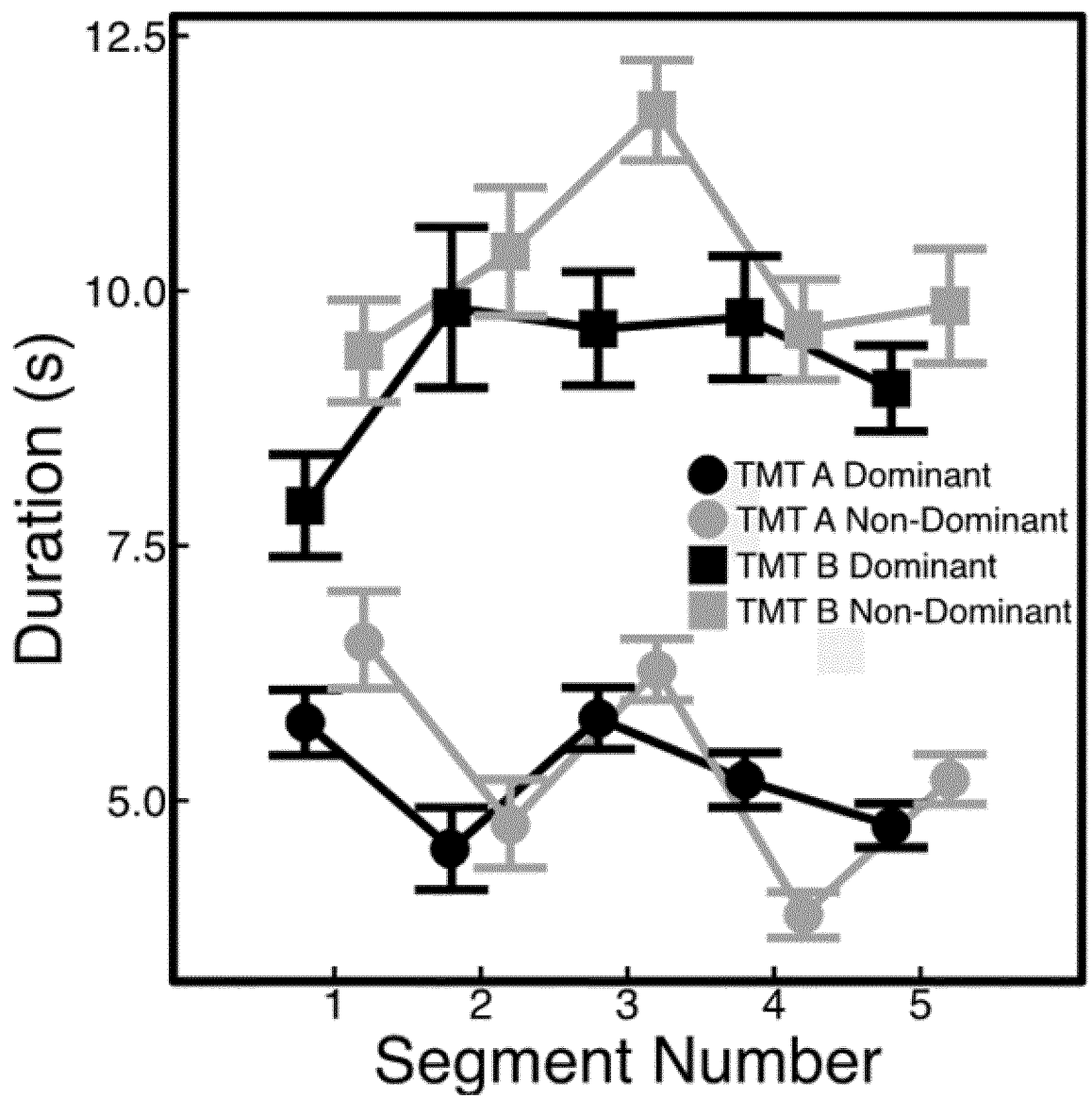
FIG. 16 shows the mean completion time per segment for both TMT A and B for the dominant and the non-dominant hand condition.

In order to have a more complete understanding of why the differences between the dominant (right) and non-dominant (left) hand occur on TMT B, we analyzed completion time over TMT segments as defined by Poreh et al. (2012). Both TMT A and B were divided into five segments each consisting of five elements, i.e. segment one consists of elements 1 to 5 (A) and elements 1 to 3 (B), segment two consists of elements 6 to 10 (A) and elements C to E (B), segment three consists of elements 11 to 15 (A) and elements 6 to 8 (B), segment four consist of elements 16 to 20 (A) and elements H to J (B), and segment five consists of elements 21 to 25 (A) and elements 11 to 13 (B). Prior research has shown that on TMT A, participants are fastest on the first segment and slowest on the third segment and on TMT B, participants are fastest on the first segment, slower on segments 3 and 4 and then faster again on segment 5 (Poreh, Miller, Dines, & Levin, 2012). FIG. 16 shows the mean completion time per segment for both TMT A and B for the dominant (black symbols) and the non-dominant (yellow/grey symbols) hand condition. Round symbols refer to the TMT A, square symbols to the TMT B. Error bars are standard errors of the mean. A mixed ANOVA with condition as between-subject factor and segment as within-subject factor shows a significant interaction effect between condition and segment ($F(2.819, 20.426)=4.614$, $p=0.005$) for TMT A. On TMT B, a mixed ANOVA shows a significant main effect of segment ($F(3.534, 54.104)=5.492$, $p=0.001$) and no interaction effect between condition and segment ($F(3.534, 17.802)=1.807$, $p=0.136$). The difference between the two conditions shows a trend ($F(1, 80)=3.264$, $p=0.075$). These findings suggest that the difference between the dominant and non-dominant hand condition on TMT B is due to a general slowing across the TMT B rather than a slowing on a specific segment of the test. In the dominant hand condition, participants show a similar pattern on TMT B as found in previous research, i.e. they are fast on the first segment, then slow down on the second, third and fourth segment and then accelerate on the last segment (Poreh et al., 2012). In the non-dominant hand condition participants show a similar pattern but are particularly slow on the third segment, although the interaction between condition and segment was not significant as mentioned above.

Figure 17:
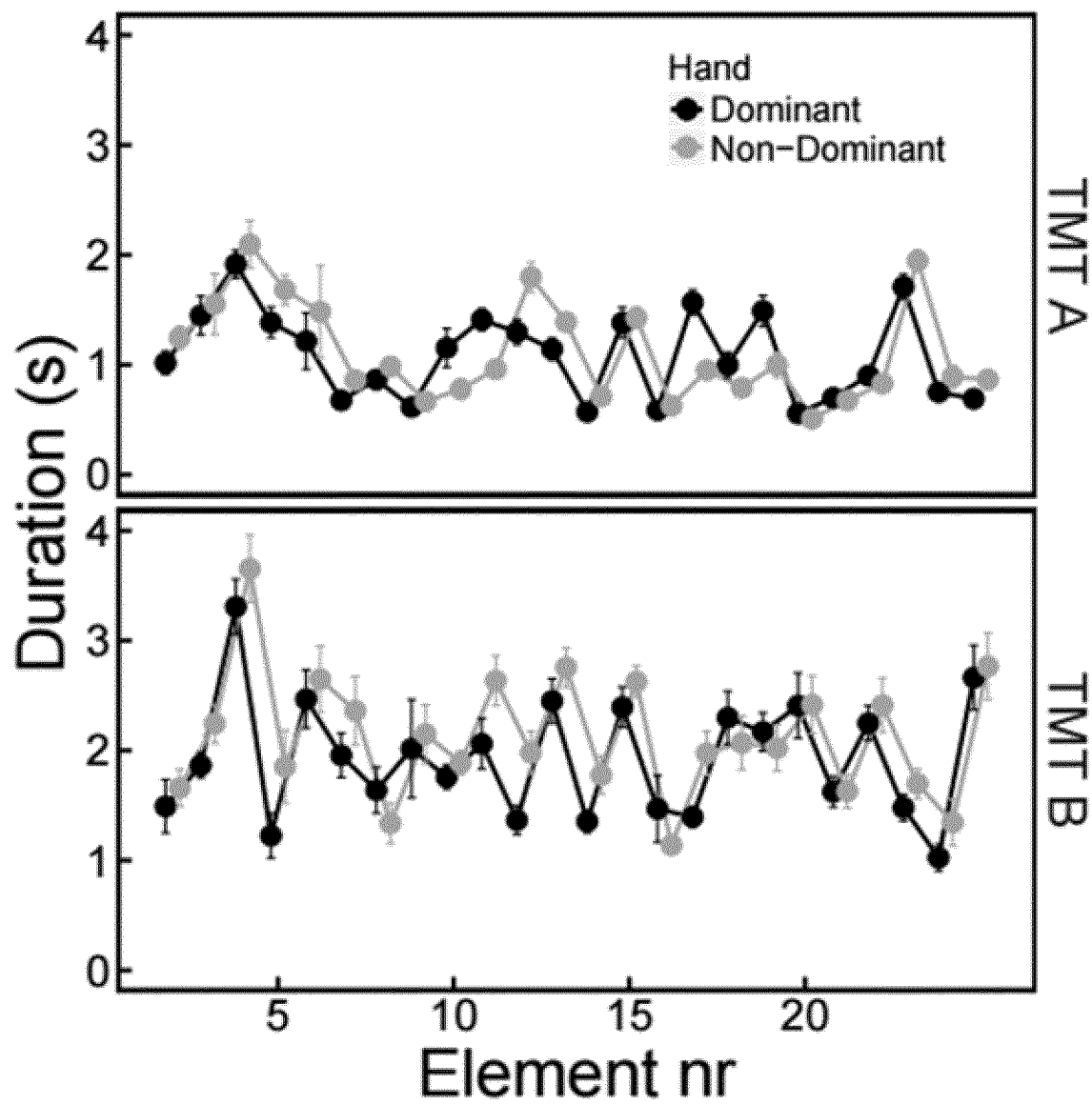
FIG. 17 shows the mean completion times per element for TMT A and B.

To gain an even more detailed understanding, we reviewed the completion times of the individual elements. In FIG. 17, the mean completion times per element are plotted for TMT A (upper panel) and B (lower panel) in both conditions for the dominant (black symbols) and non-dominant hand condition (yellow/grey symbols). Error bars are standard errors of the mean. Element numbers indicate the order number and do not refer to the content of the elements. On both parts of the TMT, some elements are completed faster than others which may indicate that these elements have different physical properties or require different cognitive processes. Moreover, it can be seen that on both TMTs some elements are completed faster with one hand than with the other. On the TMT A, the dominant (right) hand is particularly fast relative to the non-dominant (left) hand on elements 5, 6 (segment 1 and 2), 12 and 13 (segment 3), whereas the non-dominant (left) hand is particularly fast on elements 10 (segment 2), 11 (segment 3), 17 and 19 (segment 4).

Figure 18:
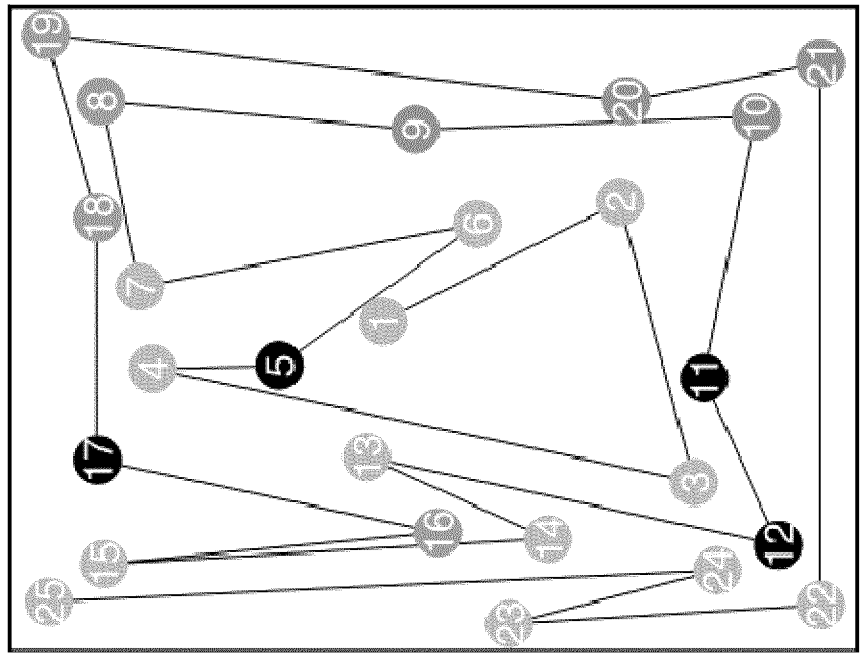
FIG. 18 shows the completion times per element for TMT A and B.
Figure 18:
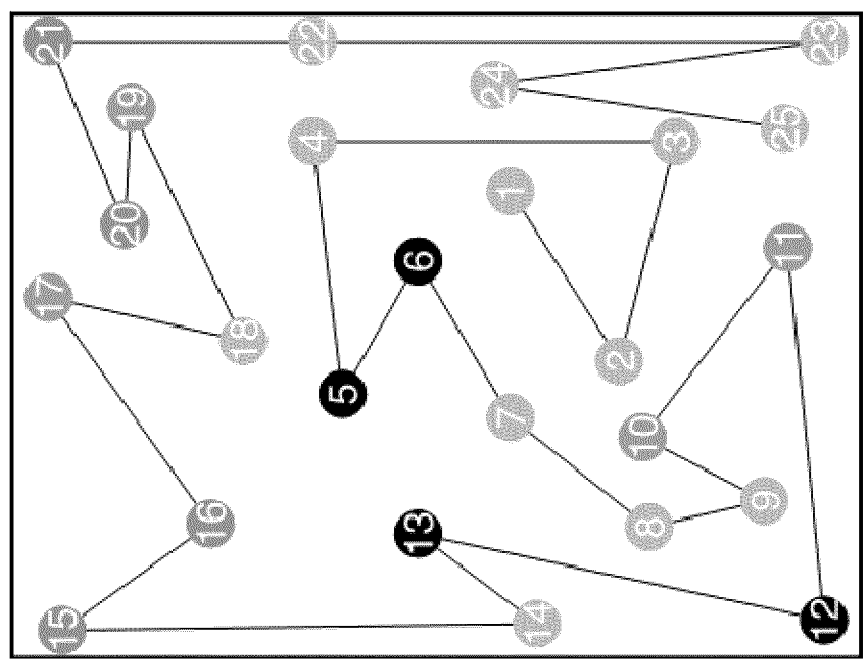

FIG. 18 shows the elements with the biggest difference in completion times between the two conditions. In particular, FIG. 18 shows the completion times per element for TMT A (left) and B (right). The black elements (elements 5, 6, 12, 13 in TMT A, elements 5, 11, 12, 17 in TMT B) are the ones on which the dominant (right) hand was faster and the orange elements (elements 10, 11, 17, 19 in TMT A, elements 8, 16, 18, 19 in TMT B) are the ones on which the non-dominant (left) hand was faster. FIG. 18 shows, for TMT A and B, all orange elements are on the right of the preceding element, while five of the eight black elements are on the left of the preceding element. On the TMT B, the elements that were completed fastest with the non-dominant (left) hand—relative to the dominant (right) hand—were elements 8 (segment 1), 16, 18 and 19 (segment 4). They are all situated to the right of the preceding element except for element 16. Elements 5 (segment 1), 11, 12 (segment 3) and 17 (segment 4) were completed faster with the dominant (right) hand of which elements 5, 11 and 12 are clearly to the left of the preceding element.

The location of the elements with different completion times between the two conditions seems to be systematic to some extent. The most likely reason is that with the one hand the element can be freely viewed, whereas it is blocked from view by the other hand. For some of the elements, there is virtually no difference between the two conditions. The differences are smallest for the elements in green (elements 15, 16, 20, 21 in TMT A, elements 9, 10, 20, 21 in TMT B). For the TMT A these are elements 15 (segment 1), 16, (segment 2) 20, and 21 (segment 3), and for TMT B these are elements 9, 10 (segment 2), 20, and 21 (segment 4).

Inter-Element Variability

The TMT measures executive functioning. We found that non-dominant hand use had a larger negative effect on TMT B performance than on TMT A performance. An important question to address is whether this is due to interference of hand use with executive functions or whether there is an alternative explanation.

In the scientific literature and in clinical neuropsychology, there is growing interest in intra-individual variability (IIV; e.g. MacDonald, Nyberg, & Backman, 2006; MacDonald, Li, & Backman, 2009; Schretlen, Munro, Anthony, & Pearlson, 2003; Strauss, Bielak, Bunce, Hunter, & Hultsch, 2007; Tanner-Eggen, Balzer, Perrig, & Gutbrod, 2015; West, Murphy, Armilio, Craik, & Stuss, 2002). The majority of research on IIV has focused on variability in reaction time tasks where IIV refers to changes in reaction time data within an individual on a particular task rather than the mean reaction time. In clinical neuropsychology, mean completion time is a more typical outcome measure. IIV gives an indication about an individual's consistency across a task or multiple tasks or multiple sessions and can therefore provide additional information about the individual's cognitive function. The reason for the growing interest in the field of neuropsychology in IIV is that this measure is considered an informative measure of cognitive functioning and may be even more informative than overall reaction (or completion) time as it is more highly correlated with cognitive dysfunction than overall reaction time when patients are engaged in cognitively demanding tasks involving working memory and set-switch (MacDonald et al., 2006; MacDonald et al., 2009; Strauss et al., 2007; West et al., 2002). In a clinical context, IIV may provide more insight into the cognitive status of patients and allow for more accurate interpretation of test outcomes (Schretlen et al., 2003; Tanner-Eggen et al., 2015). A tests outcome may appear normal when looking at the overall completion time, We adopted a measure to explore the difference in behavior on the TMT B between conditions and the groups with a fast and slow TMT A performance to get more insights into the effect of hand-use on TMT B performance.

Reaction time tasks consist of many trials and because there are multiple measurements per individual, IIV can be calculated. With the standard pen-paper TMT there is no way to get insight into the variability in performance of an individual participant because only overall completion time is measured. However, with completion times per element derived from the digital pen recordings a measure can be calculated, a measure we call the inter-element variability (IEV). First, a distribution was compiled of the completion times per participant for all elements on the TMT B resulting in distributions of 24 completion times (the first element is not taken into account). Next, IEV was calculated as the difference between the 10% and 90% cuts through the distribution as is done to calculate IIV in reaction time tasks. Because the completion times are determined by the participant but also by element characteristics (e.g. the time needed to find visual information is dependent on its visual eccentricity and the distance to neighboring information, e.g. Vlaskamp, Over, & Hooge, 2005), the element completion times need to be normalized prior to further processing. Normalization was done by dividing each individual element completion time by the median completion time for each element across participants within a condition. These normalized completion times were then used to calculate IEV.

Figure 19:
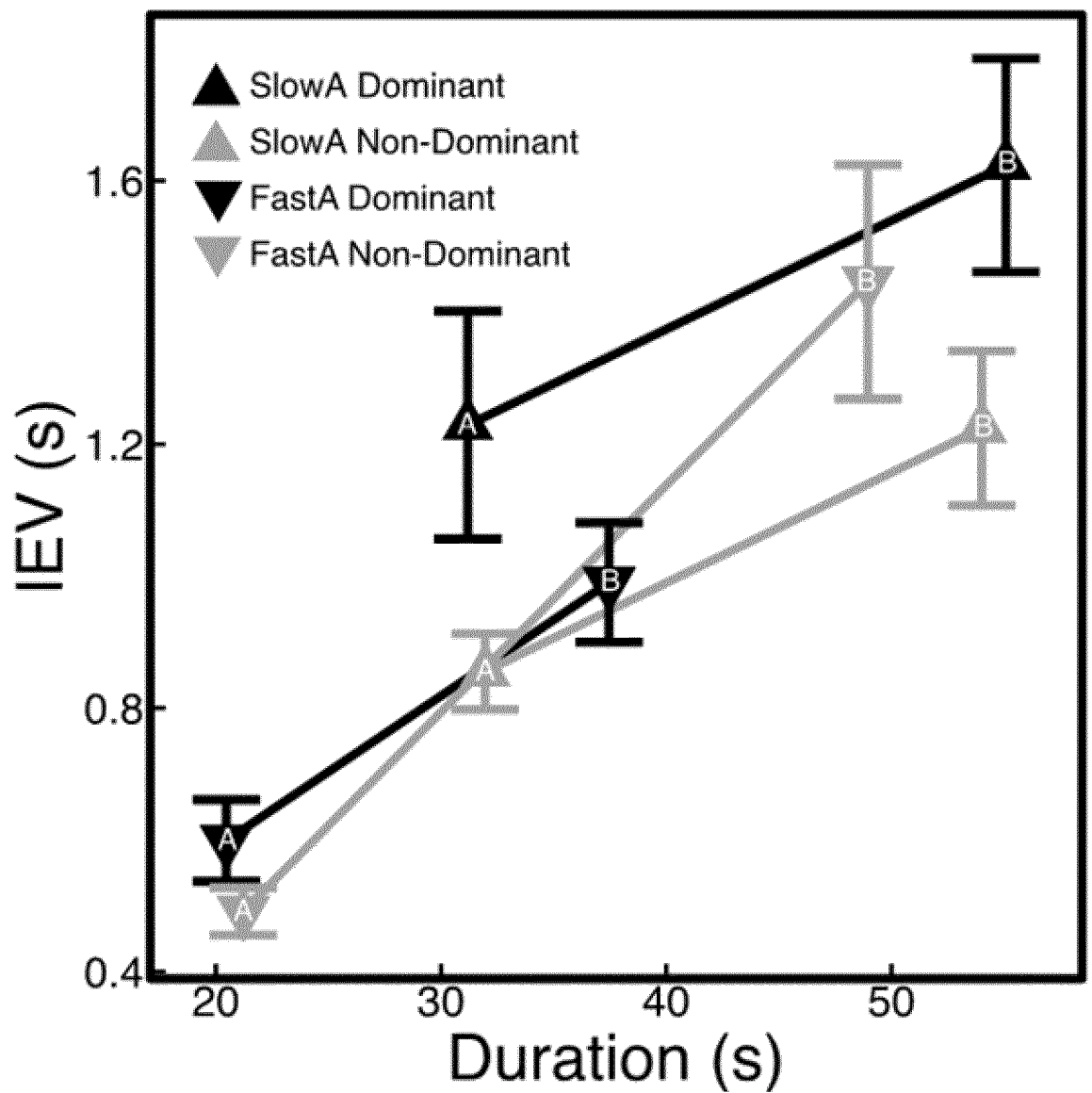
FIG. 19 shows the inter-element variability as a function of mean TMT duration.

FIG. 19 shows the inter-element variability as a function of mean TMT duration. The four lines connect TMT A and B performance for each of the groups. The letters in the symbols indicate the TMT version. The change in IEV from TMT A to TMT B is strikingly different for the fast TMT A non-dominant hand group. Thus, in FIG. 19, the mean IEV is shown for the four groups (fast/slow TMT A, dominant/non-dominant hand) on both the TMT A and the TMT B. As can be seen, IEV increases from the TMT A to the TMT B. This is expected because part B of the TMT requires more executive resources than part A. In addition, it is known from reaction time data that variability increases as reaction time increases (Wagenmakers & Brown, 2007). As can be seen, all slopes are roughly similar, except for the slope of the participants in the non-dominant hand condition who were fast on the TMT A. An independent samples t-test comparing this group to the other three groups revealed a significant difference (t(78)=−3.217, p=0.002). The slope of the non-dominant fast TMT A group is steeper than the slopes of the other three groups. This indicates that for this group, the IEV increased more from TMT A to TMT B than in the other three groups which suggests that the executive load from TMT A to TMT B increased more relative to the other groups. This finding provides additional support for our hypothesis that non-dominant hand use increases the executive demands of the TMT as IEV is higher the fast TMT A non-dominant hand group.

Interference of Non-Dominant Hand Use with Specific Cognitive Processes

The TMT B introduces a set-switching task which causes an increment in completion time relative to the TMT A which is assumed to be due to increased executive demands. However, performing the TMT also involves other (cognitive) tasks such as visual search and moving the pen from one element to the next, tasks which are mostly related to the layout of the TMT. Even though the TMT A and B have not been designed to differ on these tasks, they have been shown to differ on visual search and motor speed demands (Gaudino et al., 1995) which leaves open the possibility that for some individuals reduced completion times on the TMT B are related to other than executive functions.

Here, we sought further evidence that non-dominant hand use interferes with executive processes on the TMT B by explicitly separating the contribution of executive processes from the contribution of layout-related processes to the element completion times. For executive tasks, we assume that the processing time required for completion of each element of the TMT B is roughly equal (for sake of the argument, we ignore that there may be slight differences between elements in terms of set-switching, e.g. it may be easier to go from letters to numbers than vice versa, it may be easier to keep the first letters of the alphabet in working memory than later letters, etc.). This means that if non-dominant hand use mainly affects executive functions, the same amount of additional processing would be expected for every element completed with the non-dominant hand relative to the processing time for every element completed with the dominant hand. For tasks related to the layout of the TMT (such as visual search and motor tasks), we assume that a different amount of processing time is required for each element depending on its spatial configuration: some distances between subsequent elements are very long whereas others are short, some elements are in more cluttered areas than others and sometimes there are elements positioned in between subsequent elements. These factors are known to have a large impact on tasks such as visual search (Vlaskamp, Over & Hooge, 2005) and motor processes. Based on this assumption, an interference of non-dominant hand use with layout-related processes would be particularly noticeable on elements that already require long processing times with the dominant hand.

FIG. 7 shows the median completion times for each element of the TMT B in the non-dominant hand condition plotted against the median completion times for each element of the TMT B in the dominant hand condition. The plotted times are the median times because they are more robust to extreme values than the mean. The two lines are separate regression lines for participants with a fast TMT A and a slow TMT A. The thin dashed line has a slope of 1 and indicates equal performance in both conditions. By comparing the two regression lines to this line, we can infer whether non-dominant hand use primarily affects layout-related or executive processes. If non-dominant hand use primarily affected layout-related processes, the fitted regression lines would have a slope larger than 1 because completion times in the non-dominant hand condition would go up for elements that require more time to process. This is based on the notion that also with the dominant hand completion time increases for elements that have higher demands in terms of visual and motor processing. If on the other hand non-dominant hand use mainly affected executive functions, the lines would shift upwards relative to the dashed line but the slope would remain 1. This is based on the notion that all elements have similar completion times in terms of executive processing. As can be seen in FIG. 7, the data are most in line with the latter. Both the fast and slow TMT A groups have a slope smaller than 1. In the left part of FIG. 7, the lines are above the dashed line showing that the non-dominant hand condition was relatively slow on elements with short completion times, i.e. elements that have low visual search and motor demands. In the slow TMT A group this is averaged out by faster completion of elements with long completion times. In the fast TMT A group however, the non-dominant hand group is slower on all elements of TMT B. We determined that the reduced performance with the non-dominant hand relative to the dominant hand is not due to processes related to the layout of the TMT, but lend further support to our hypothesis that non-dominant hand use mainly affects executive functions and therefore interferes with TMT B performance.

Discussion and Conclusion

Use of the non-dominant hand affects performance on the TMT. Hand use was found to increase completion time on the TMT B but not on the TMT A. As a consequence, non-dominant hand use also affects clinically relevant measures such as the B/A ratio. Based on detailed analyses of completion times for individual elements of the TMT B, we found evidence for our hypothesis that this decrease in performance on the TMT B is related to non-dominant hand use affecting executive functions thereby interfering with TMT B completion. As described above, in contrast to TMT A which mainly reflects visual search and motor speed skills, completion of TMT B also requires higher order cognitive resources. Based on our findings, non-dominant hand use seems to compete for the same limited cognitive resources which results in a decrease in completion time on the TMT B. Interestingly, the findings reveal that in a subgroup of participants who completed the TMT with their non-dominant hand, i.e. participants who were fast on the TMT A, use of the non-dominant hand had a disproportionally large effect on TMT B performance that cannot be explained by demographic variables. We will discuss the outcomes and the clinical relevance in more detail below.

Clinical Relevance

It is important to have more insights into TMT performance with the non-dominant hand since patients who are unable to use their dominant hand may perform the test with their non-dominant hand and there is currently limited knowledge about how non-dominant hand use affects performance. The findings of this study clearly show that TMT completion times and derived scores like the B/A ratio need to be interpreted with caution if a patient uses his non-dominant hand to avoid false attribution of increased completion time and derived scores to cognitive deficits. As the results show, an abnormal test performance may be caused by using the non-dominant hand which in our study resulted in a mean difference of almost 5 seconds on the TMT B which is higher than a difference of 1.9 seconds found in previous research (LoSasso et al., 1998). A difference of 5 seconds seems clinically relevant when comparing it to existing norm scores for the TMT (e.g. Tombaugh, 2004). The difference in mean completion time for TMT B between age groups 35 to 44 and 45 to 54 is about 5 seconds. An increase in 5 seconds among individuals between 35 and 44 is equal to at least a 10% drop in percentile when scoring in the 30% percentile or better (Tombaugh, 2004). When looking specifically at people who were fast on the TMT A, the effect of using the non-dominant hand becomes even more pronounced. Using the non-dominant hand increased completion time by 11 seconds in this subgroup. An 11 second increase in completion time on the TMT B is close to the difference in completion time between the age groups 25 to 34 and 45 to 54, i.e. age groups that are 20 years apart. An increase in 11 seconds among individuals between 35 and 44 is equal to at least a 20% drop in percentile when scoring in the 30% percentile or better (Tombaugh, 2004).

Furthermore, in our sample of healthy individuals, four participants scored on or above the B/A ratio cut-off score of 3 when they performed the TMT with their non-dominant hand. This was due to a particularly fast completion time on TMT A and a slow completion time on TMT B. Based on their ratio score, these participants would have been considered to have a deficit when in fact their abnormal score was due to use of the non-dominant hand.

Digital Parameters

In the present study, TMT performance was measured digitally. The importance of digital measurement of cognitive function has been highlighted by others (Bauer et al., 2012; Poreh et al., 2012; Salthouse & Fristoe, 1995; Schatz & Browndyke, 2002; Woods et al., 2015) as it allows for a more accurate and more standardized assessment of cognitive function. Moreover, a digital TMT allows for the recording of additional measures that may provide relevant information that is missed in the current paper-pencil version of the test such as a segment-by-segment and element-by-element analysis of the TMT. Research in this area shows that more detailed analyses of additional parameters provides valuable information (Poreh et al., 2012; Salthouse & Fristoe, 1995; Woods et al., 2015) which is confirmed by the findings of our study. By looking at the total completion times for TMT A and B, we found support for our hypothesis that non-dominant hand use interferes with performance of the TMT B but not the TMT A because completion of TMT B and non-dominant hand use draw on the same limited cognitive resources. The detailed analysis of the completion times for individual elements of the TMT B provides additional support for this hypothesis by showing that non-dominant hand use mainly affects executive functions rather than layout-related processes and therefore interferes with TMT B performance.

Even though our findings show that a slowing in performance on the TMT B with the non-dominant hand is not due to layout-related processes, the element-by-element analysis revealed that some elements were completed faster than others. Generally, elements that are located to the right of the preceding element were completed faster with the left hand and elements that are located left to the preceding element were completed faster with the right hand. This is probably due to the position of the hand and the fact that the hand obstructs the view of certain elements during completion of the TMT. Our analysis revealed that on both the TMT A and the TMT B, the number of elements on which the dominant hand is faster than the non-dominant hand is the same as the number of elements on which the non-dominant hand is faster than the dominant hand. However, it may be expected that if targets are obstructed by the non-dominant (left) hand, since motor control of the non-dominant hand is less automatic than motor control of the dominant hand, moving the non-dominant hand requires more cognitive resources which increases the cognitive load of the task. Even though we did not explore this specifically, based on these insights, it seems possible that the TMT is biased for a specific hand and more research into this seems valuable.

The detailed analyses of the B/A ratio scores allowed us to obtain more insights into the underlying reasons for a high B/A ratio score in a subgroup of participants. As described, a subgroup of participants had a particularly high B/A ratio score which in clinical practice is considered an indication of set-switching impairments. By determining the IEV based on individual element completion times, we were able to demonstrate that the increased B/A ratio with the non-dominant hand was related to a general increase in element completion times and not to a slowing on a subset of elements. This is interesting because it may be assumed that use of the non-dominant hand would slow down performance on specific elements, e.g. those that succeed elements that are to the left of preceding elements because they are obstructed by the left hand or those in the second half of the test because it may be more difficult to keep later letters of the alphabet in working memory than the first letters of the alphabet due to familiarity. However, even though the element-by-element analysis provides some evidence for these effects, the increase in TMT B completion time in the subgroup of participants who performed the TMT with the non-dominant hand and had a fast completion time on TMT A was due to a general increment in element completion times and not to a slowing on a subset of elements. IEV provides additional insights into the consistency of an individual's behavior across the TMT. IEV is analogous to IIV in computerized reaction time tasks used in experimental psychology and could be a new interesting outcome measure of a computerized TMT. As described above, there is growing interest in performance variability as an additional outcome measure since it may provide additional information and may be even more informative than overall completion times as it is more highly correlated with cognitive dysfunction than reaction time when patients are engaged in cognitively demanding tasks involving working memory and set-switch (MacDonald et al., 2006; Strauss et al., 2007; West et al., 2002).

A possible explanation is that the strategy used by this group to complete TMT A did not work as well on TMT B. It may be that some individuals used a strategy that is mostly focused on speed, while others used a strategy that is not focused on speed. The IEV data indicate that both strategies work well for both the TMT A and the TMT B when it is completed with the dominant hand, i.e. individuals' behavior is consistent across both parts of the TMT. It furthermore seems from these data that the non-speed strategy works well when performing the TMT with the non-dominant hand, i.e. the behavior of participants in the slow TMT A non-dominant hand group also shows consistent behavior across both parts of the TMT. The fast TMT A non-dominant hand group does however does not show consistent behavior.

As the detailed analyses demonstrate, digital measurement clearly provides the opportunity for exploration of specific underlying processes which contributes to a more complete understanding of how non-dominant hand use affects TMT B completion. In general, we strongly believe that even though at present clinical neuropsychological assessments are conducted in a paper-pencil based format, we believe based on our research that there is a benefit to performing neuropsychological tests on a digital medium. It is however important to note that although digital neuropsychological assessment offers various benefits, there are a number of important issues to consider such as the need to establish the psychometric properties of new digital measures (Bauer et al., 2012; Schatz & Browndyke, 2002), the need to understand potential technological complications and limitations (Bauer et al., 2012; Cernich, Brennana, Barker, & Bleiberg, 2007) as well as the need to provide methodological detail regarding computer-based assessment measures to enable replication which eventually contributes to confidence in system and method (Schatz & Browndyke, 2002). We believe that our research contributes to the growing body of research on digital measurement of cognitive function by demonstrating the added value of digital measurement of the TMT.

Conclusion

Use of the non-dominant hand affects performance on the TMT. Performing part B of the TMT with the non-dominant hand increases completion time since both the sensorimotor task (using the non-dominant hand) and the cognitive task itself require similar limited cognitive resources. Our study hints at important clinical consequences of using the non-dominant hand. Specifically, use of the non-dominant hand can have a major impact on clinical outcomes such as the B/A ratio. A B/A ratio score close to or higher than 3 could be falsely attributed to cognitive dysfunction whereas at least in some cases a high B/A ratio score is due to performing the test with the non-dominant hand.

We demonstrated the importance of a more detailed analysis of TMT performance which is possible when measuring TMT performance digitally. A more detailed analysis of the different components of the TMT can be used to better interpret specific outcomes and may eventually be used to improve the reliability of the TMT.

The invention claimed is:

1. A computer-implemented method for determining an indication of cognitive impairment of a subject during or following a test comprising a plurality of targets that are to be completed by the subject, the method comprising the steps of:
    receiving information on time taken to complete each of the plurality of targets by the subject;
    determining a regression line for the subject as a linear fit of the received information on time taken to complete each of the plurality of targets plotted against information on time taken to complete each of the plurality of targets for a reference group of subjects;
    performing at least one of the following determining steps:
        determining that the subject has an indication of visual attention/motoric dysfunction based on a slope of the determined regression line; and
        determining that the subject has an indication of executive cognitive dysfunction based on an offset of the determined regression line; and
    outputting at least one of the indication of whether the subject has visual attention/motoric dysfunction and the indication of whether the subject has executive cognitive dysfunction.

2. A method as claimed in claim 1, wherein the information on time taken to complete each of the plurality of targets by the subject comprises, for each target, time from completion of a preceding target to completion of said each target by the subject.

3. A method as claimed in claim 2, wherein completion of each said target comprises the subject marking a path from said preceding target to said each target on a test surface using a marking device.

4. A method as claimed in claim 1, wherein the information on time taken to complete each of the plurality of targets for the reference group of subjects comprises, for each of the plurality of targets, an average of time taken to complete said each target by subjects in the reference group of subjects.

5. A method as claimed in claim 1, wherein the step of determining that the subject has the indication of visual attention/motoric dysfunction based on the slope of the determined regression line comprises determining if the slope of the determined regression line is greater than one.

6. A method as claimed in claim 1, wherein the step of determining that the subject has the indication of executive cognitive dysfunction comprises determining the offset of the determined regression line is greater than zero.

7. A method as claimed in claim 1, wherein the offset of the determined regression line is determined based on an average of time taken to complete each of the plurality of targets by the reference group of subjects.

8. A method as claimed in claim 1, wherein the method further comprises the step of:
    normalising time taken to complete each of the plurality of targets by the subject using information on time taken to complete the corresponding target by the reference group of subjects to provide a set of normalised times.

9. A method as claimed in claim 8, wherein the method further comprises the step of:
    determining a measure of variability of the set of normalised times.

10. A method as claimed in claim 9, wherein the method further comprises the steps of:
    determining the measure of variability of the set of normalised times for a first test by the subject;
    determining a measure of variability of the set of normalised times for a second test by the subject; and
    determining a further indication of the visual attention/motoric dysfunction of the subject and/or a further indication of executive cognitive dysfunction of the subject from a comparison of the determined measure of variability of the set of normalised times for the first test and determined measure of variability of the set of normalised times for the second test.

11. A method as claimed in claim 1, wherein the plurality of targets comprises a set of number targets and a set of letter targets; and wherein the method further comprises the step of:
    determining an indication of literary dysfunction of the subject based on a comparison of time taken to complete each of the set of number targets and the time taken to complete each of the set of letter targets.

12. A method as claimed in claim 11, wherein the step of determining the indication of literary dysfunction of the subject comprises:
    determining an average time taken to complete each of the set of number targets;
    determining an average time taken to complete each of the set of letter targets; and
    determining the indication of the literary dysfunction of the subject based on a difference between determined averages and/or based on a ratio of determined averages.

13. A method as claimed in claim 12, wherein the step of determining the indication of the literary dysfunction of the subject comprises comparing a difference between determined averages to a difference between averages for the reference group of subjects and/or comparing the ratio of determined averages to a ratio of averages for the reference group of subjects.

14. A computer program product comprising a non-transitory computer readable medium having computer readable code embodied therein, the computer readable code being configured such that, on execution by a processor, the processor is caused to perform the method of claim 1.

15. An apparatus for determining of cognitive impairment of a subject during or following a test comprising a plurality of targets that are to be completed by the subject, the apparatus comprising:

a processor that is configured to:

receive information on time taken to complete each of the plurality of targets by the subject;

determine a regression line for the subject as a linear fit of the received information on time taken to complete each of the plurality of targets plotted against information on time taken to complete each of the plurality of targets for a reference group of subjects;

determine that the subject has an indication of visual attention/motoric dysfunction based on a slope of the determined regression line and/or determine that the subject has an indication of executive cognitive dysfunction based on an offset of the determined regression line; and output the indication of whether the subject has visual attention/motoric dysfunction and/or the indication of whether the subject has executive cognitive dysfunction.

16. An apparatus as claimed in claim 15, wherein the apparatus further comprises:

a display screen for displaying the plurality of targets to the subject; and a user interface for receiving an input from the subject to complete one or more of the plurality of targets.

17. An apparatus as claimed 16, wherein the display screen and the user interface are a touchscreen.

18. An apparatus as claimed in claim 15, wherein the apparatus further comprises:

a receiver for receiving the information on time taken to complete each of the plurality of targets by the subject from an electronic device.

19. An apparatus as claimed in claim 15, wherein the processor is configured to determine that the subject has the indication of visual attention/motoric dysfunction based on the slope of the determined regression line by determining if the slope of the determined regression line is greater than one.

20. An apparatus as claimed in claim 15, wherein the processor is configured to determine that the subject has the indication of executive cognitive dysfunction by determining if the offset of the determined regression line is greater than zero.

* * * * *